United States Patent
Huang et al.

(10) Patent No.: US 11,192,857 B2
(45) Date of Patent: Dec. 7, 2021

(54) 2-ETHYLIDENE-1,5-DIMETHYL-3,3-DI-PHENYLPYRROLIDINE ANALOGS AND METHODS FOR THEIR SYNTHESIS AND USE

(71) Applicant: ALERE SAN DIEGO, INC., San Diego, CA (US)

(72) Inventors: Fei Huang, San Diego, CA (US); Dongpei Wu, San Diego, CA (US); Lupe Mejorado, San Diego, CA (US); Mariusz Banaszczyk, San Diego, CA (US)

(73) Assignee: ALERE SAN DIEGO, INC., San Diego, CA (US)

( * ) Notice: Subject to any disclaimer, the term of this patent is extended or adjusted under 35 U.S.C. 154(b) by 105 days.

(21) Appl. No.: 16/302,573

(22) PCT Filed: May 18, 2017

(86) PCT No.: PCT/US2017/033373
§ 371 (c)(1),
(2) Date: Nov. 16, 2018

(87) PCT Pub. No.: WO2017/201314
PCT Pub. Date: Nov. 23, 2017

(65) Prior Publication Data
US 2019/0292148 A1     Sep. 26, 2019

Related U.S. Application Data

(60) Provisional application No. 62/338,448, filed on May 18, 2016.

(51) Int. Cl.
*C07D 207/20*    (2006.01)
*A61K 39/385*    (2006.01)
(Continued)

(52) U.S. Cl.
CPC ........ *C07D 207/20* (2013.01); *A61K 39/385* (2013.01); *C07D 207/267* (2013.01);
(Continued)

(58) Field of Classification Search
CPC ........ A61K 39/385; A61K 2039/6081; C07D 207/267; C07D 409/12; C07D 403/12;
(Continued)

(56) References Cited

U.S. PATENT DOCUMENTS

| | | | | |
|---|---|---|---|---|
| 5,710,256 A | * | 1/1998 | Buechler | ........... C07C 323/59 530/300 |
| 6,140,137 A | * | 10/2000 | Sigler | ........... C07D 207/20 435/188 |
| 2007/0129434 A1 | | 6/2007 | Smith-Carliss et al. | |

FOREIGN PATENT DOCUMENTS

| | | | | |
|---|---|---|---|---|
| EP | 0931062 B1 | * | 11/2004 | ........ G01N 33/9486 |
| EP | 2308848 | | 4/2011 | |
| WO | 199854133 A1 | | 12/1998 | |

OTHER PUBLICATIONS

International Search Report and Written Opinion dated Aug. 24, 2017 in PCT/US2017/033373 (10 pages).
(Continued)

*Primary Examiner* — Shafiqul Haq
(74) *Attorney, Agent, or Firm* — Casimir Jones, S.C.; Anne M. Reynolds

(57) ABSTRACT

The present invention relates to novel 2-ethylidene-1,5-dimethyl-3,3-diphenylpyrrolidine analogs, and methods for their synthesis and use. Such analogs are designed to provide a convenient linkage chemistry for coupling under mild conditions to a suitable group on a target protein, polypeptide, solid phase or detectable label.

13 Claims, 2 Drawing Sheets

(51) Int. Cl.
*C07K 16/44* (2006.01)
*G01N 33/94* (2006.01)
*C07D 207/267* (2006.01)
*C07D 403/12* (2006.01)
*C07D 409/12* (2006.01)
*A61K 39/00* (2006.01)

(52) U.S. Cl.
CPC ......... *C07D 403/12* (2013.01); *C07D 409/12* (2013.01); *C07K 16/44* (2013.01); *G01N 33/9486* (2013.01); *A61K 2039/6081* (2013.01); *C07K 2317/33* (2013.01)

(58) Field of Classification Search
CPC .................. C07D 207/20; C07K 16/44; C07K 2317/33; G01N 33/9486; A61P 25/04
See application file for complete search history.

(56) References Cited

OTHER PUBLICATIONS

Extended European Search Report; EP17800185.5 dated Feb. 27, 2020, 12 pages.

\* cited by examiner

2-ETHYLIDENE-1,5-DIMETHYL-3,3-DIPHENYL-PYRROLIDINE ANALOGS AND METHODS FOR THEIR SYNTHESIS AND USE

The present invention is filed under 35 U.S.C. § 371 as the U.S. national phase of International Patent Application No. PCT/US2017/033373, filed May 18, 2017, which designated the United States and claims priority to U.S. Provisional Application No. 62/338,448 filed May 18, 2016, each of which is hereby incorporated by reference in its entirety including all tables, figures, and claims.

FIELD OF THE INVENTION

The present invention relates to novel 2-ethylidene-1,5-dimethyl-3,3-diphenylpyrrolidine analogs useful for preparing conjugates comprising, inter alia, proteins, polypeptides, and labels; to conjugates comprising such analogs, and to methods for their synthesis and use.

BACKGROUND OF THE INVENTION

The following discussion of the background of the invention is merely provided to aid the reader in understanding the invention and is not admitted to describe or constitute prior art to the present invention.

Methadone is an opioid used to treat pain and as maintenance therapy or to help with detoxification in people with opioid dependence. Methadone is metabolized relatively slowly in the liver to EDDP and a related compound 2-ethyl-5-methyl-3,3-diphenyl-1-pyrroline (EMDP). Methadone has a typical elimination half-life of 15 to 60 hours with a mean of around 22 hours. However, metabolism rates vary greatly between individuals, up to a factor of 100, ranging from as few as 4 hours to as many as 190 hours. This variability is apparently due to genetic variability in the production of the enzymes involved in that metabolism, CYP3A4, CYP2B6 and CYP2D6. Many substances can also induce, inhibit or compete with these enzymes further affecting (sometimes dangerously) methadone half-life.

Methadone and its major metabolite, 2-ethylidene-1,5-dimethyl-3,3-diphenylpyrrolidine (EDDP) are often measured in urine, plasma or serum as part of a drug abuse testing program, to confirm a diagnosis of poisoning in hospitalized victims, criminal investigations, and in post-mortem examinations.

In developing a binding assay for EDDP or EMDP, the artisan must consider that samples may contain these metabolites of opiates/opioids including the closely related methadone parent compound. Thus, immunogenic and label conjugates should be designed to present EDDP or EMDP so as to provide an assay with minimal cross-reactivity to other opioids. Analogs for use in preparing such conjugates should also be designed to provide convenient attachment to various proteins, polypeptides, and labels under mild conditions.

BRIEF SUMMARY OF THE INVENTION

It is an object of the invention to provide novel EDDP and EMDP analogs, and methods for their synthesis and use. Such analogs preferably provide a linkage chemistry for convenient coupling to a suitable group on a target protein, polypeptide, or label.

Thus, EDDP and EMDP have the following structures:

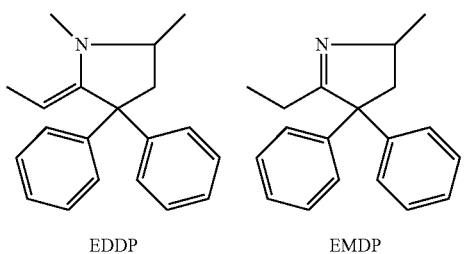

EDDP      EMDP

In a first aspect, the invention relates to compounds, or salts thereof, having a general formula selected from (I), (II), (III), (IV), or (V):

(IH)

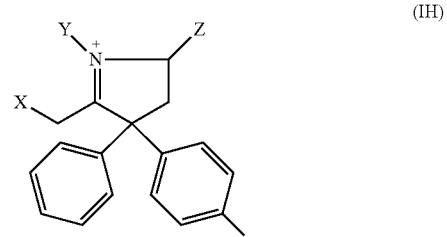

(II)

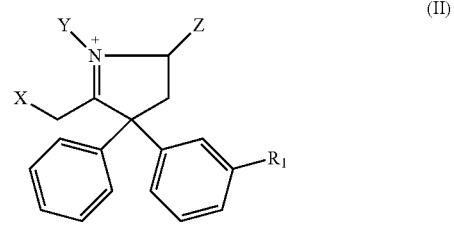

(III)

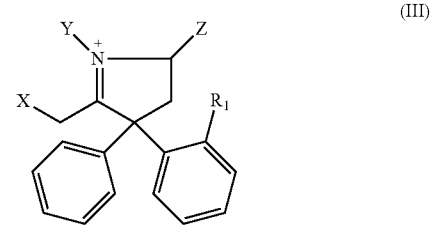

(IV)

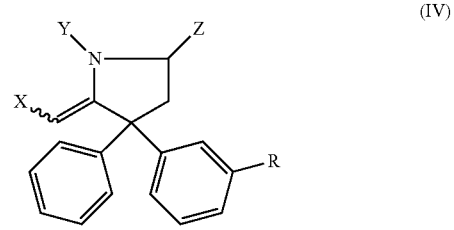

(V)

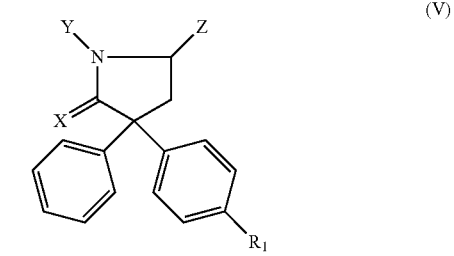

wherein R and R1 are each —CH$_2$—R2, where R2 is a linkage chemistry which provides a terminal functional moiety selected from the group consisting of protected or unprotected sulfhydryl moieties, protected or unprotected amine moieties, primary amine-reactive moieties, sulfhydryl-reactive moieties, photoreactive moieties, carboxyl-reactive moieties, arginine-reactive moieties, and carbonyl-reactive moieties;

X is H, N, O, C$_{1-6}$ saturated alkyl straight or branched chain, C$_{1-6}$ unsaturated alkyl straight or branched chain, C$_{1-6}$ alkoxy, or haloalkyl;

Y is H, C$_{1-6}$ saturated alkyl straight or branched chain, C$_{1-6}$ unsaturated alkyl straight or branched chain, C$_{1-6}$ alkoxy, or haloalkyl;

Z is H, C$_{1-6}$ saturated alkyl straight or branched chain, C$_{1-6}$ unsaturated alkyl straight or branched chain, C$_{1-6}$ alkoxy, or haloalkyl.

Preferably, R3 is a functional moiety selected from the group consisting of protected or unprotected sulfhydryl moieties, protected or unprotected amine moieties, primary amine-reactive moieties, sulfhydryl-reactive moieties, photoreactive moieties, carboxyl-reactive moieties, arginine-reactive moieties, and carbonyl-reactive moieties. Most preferably, the functional moiety is selected from the group consisting of a maleimide, an alkyl halide, an aryl halide, an alpha-haloacyl, a pyridyl disulfide, a carbonyl, a carboxyl, a thiol, a thioester, disulfide, or a cyclic thiolactone.

In certain preferred embodiments, R2 is —(CH$_2$)$_n$R3, wherein n is 0 to 6. In various embodiments, R2 is —(CH$_2$)$_{1-4}$—S—C(O)—CH$_3$, —(CH$_2$)$_{1-4}$—C(O)—OH, —(OCH2CH2)n-R3 where n is between 0 and 25, or

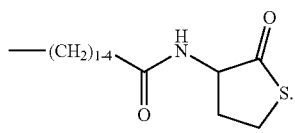

In certain embodiments, the compound is selected from the group consisting of

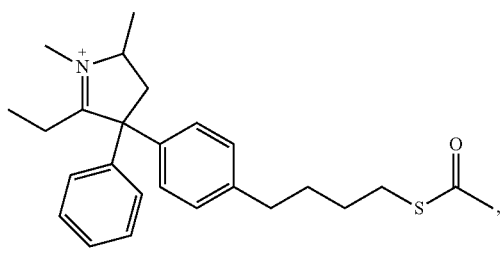

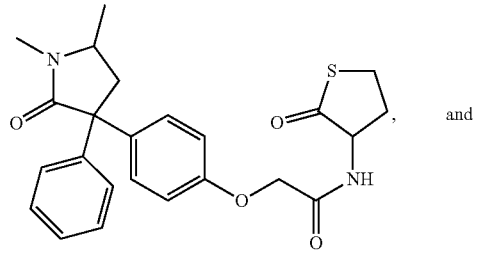

-continued

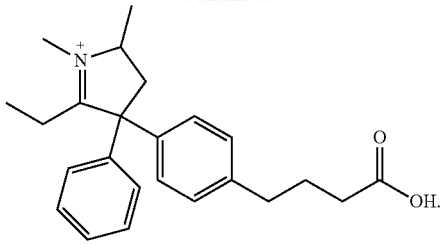

In a related aspect, the invention relates to compositions comprising one or more of the foregoing compounds (or their salts) covalently bound through the functional moiety on the compound(s) to a corresponding coupling site on a protein, polypeptide, detectable label, nucleic acid, or solid phase, referred to herein as "EDDP conjugates."

The compounds of the present invention may be directly linked to an appropriate target protein, polypeptide, label, or other molecule to form a conjugate via a coupling group naturally occurring in the target molecule, or by adding a coupling group to the target molecule. Exemplary coupling groups are described hereinafter, and methods for incorporating such coupling groups into target molecules for conjugation to the compounds described above are well known in the art. In the case of compounds of the invention comprising a protected functional moiety, removal of the protective group is performed by methods known in the art.

In certain embodiments, the compounds comprise a functional moiety that is sulfhydryl-reactive, such as a maleimide, an alkyl halide, an aryl halide, an acryl, or an α-haloacyl. The sulfhydryl-reactive moiety preferably reacts with sulfhydryls on the target protein, polypeptide, label, or other molecule to form thiol ether bonds. Alternatively, the functional moiety may be a carbonyl-reactive moiety.

Preferred coupling groups on target molecules are maleimides, which are linked according to the following reaction scheme:

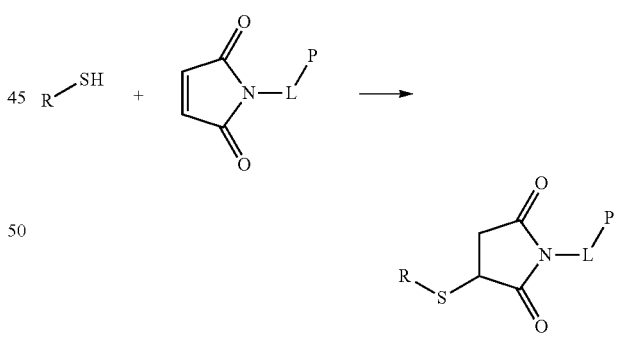

where R—SH is a compound of the invention comprising a free thiol (either as a free thiol or following deprotection of a protected thiol), L is a linkage chemistry, and P is a target protein, polypeptide, label, or other molecule. L is preferably C$_{1-10}$ alkylene straight or branched chain comprising from 0-4 backbone (i.e., non-substituent) heteroatoms, optionally substituted with from 1 to 4 substituents independently selected from the group consisting of C$_{1-6}$ alkyl straight or branched chain, —NO$_2$, —NH$_2$, =O, halogen, trihalomethyl, C$_{1-6}$ alkoxy, —OH, —CH$_2$OH, and —C(O)NH$_2$.

In certain embodiments, P is a protein, most preferably an antigenic protein which can be used to raise an immune response to an epitope on the compound of the invention using a so-called "hapten-carrier" immunogen. Common carrier proteins include bovine serum albumin, keyhole limpet hemocyanin, ovalbumin, etc. Protocols for conjugation of haptens to carrier proteins may be found in ANTIBODIES: A LABORATORY MANUAL, E. Harlow and D. Lane, eds., Cold Spring Harbor Laboratory (Cold Spring Harbor, N.Y., 1988) pp. 78-87, which is hereby incorporated by reference. Thus, in certain embodiments, one or more compounds of the present invention may be directly linked to a protein selected from the group consisting of keyhole limpet hemocyanin, bovine serum albumin, thyroglobulin, ovalbumin, lysozyme, or dextran.

In still other embodiments, one or more compounds of the present invention may be directly linked to a solid phase selected from the group consisting of a membrane, a cellulose-based paper, a polymeric particle, a latex particle, a paramagnetic particle, a gold particle, a magnetic particle, a metallic particle, a plasmonic particle, a glass substrate, a silicon substrate, a plastic substrate, and a multiple-well plate.

Alternatively, P may preferably be a detectable label. Preferred detectable labels may include molecules or larger structures that are themselves detectable (e.g., fluorescent moieties, electrochemical labels, metal chelates, latex particles, etc.), as well as molecules that may be indirectly detected by production of a detectable reaction product (e.g., enzymes such as horseradish peroxidase, alkaline phosphatase, etc.) or by a specific binding molecule which itself may be detectable (e.g., biotin, avidin, streptavidin, digoxigenin, maltose, oligohistidine, 2,4-dintrobenzene, phenylarsenate, ssDNA, dsDNA, etc.). Exemplary conjugation to such detectable labels is described hereinafter. Particularly preferred detectable labels are fluorescent or colored microspheres, such as flourescent latex particles.

The foregoing lists of suitable target molecules are not meant to be limiting. Further exemplary embodiments are described hereinafter. In addition, numerous other classes of suitable targets, including peptide hormones, therapeutic proteins, antibodies, antibody fragments, single-chain variable region fragments, small molecules, nucleic acids, oligosaccharides, polysaccharides, cyclic polypeptides, peptidomimetics, aptamers and solid phases are known in the art.

While a conjugation target may be conjugated 1:1 with a EDDP analog of the invention, an individual target may also comprise more than 1 conjugation site, and hence more than 1 compound of the invention may be conjugated thereto. In preferred embodiments, a conjugation target (e.g., a protein, peptide, or label) comprises at least 10 EDDP analog moieties covalently bound thereto, more preferably at least 30, still more preferably at least 50, and most preferably at least 100.

In still other related aspects, the present invention relates to methods for the production and use of the EDDP analogs of the present invention to form conjugates with a protein, polypeptide, label, or other molecule.

Such methods can comprise contacting one or more compounds of the invention comprising a reactive moiety (e.g., comprising a free thiol) with one or more target molecules comprising one or more corresponding coupling sites, under conditions where the reactive moiety(s) react with the coupling site(s) to form one or more conjugates. Conditions for such reactions are dependent upon the reactive moiety(s) selected, and are well known to the skilled artisan. Exemplary conditions are described hereinafter.

Such methods may further comprise the step of deprotecting a protected reactive moiety from one or more compounds of the invention prior to said contacting step, and/or attaching one or more coupling sites to a protein, polypeptide, label, or other molecule to form an appropriate conjugation target. In the latter case, this may comprise the use of bifunctional cross-linkers that provide an appropriate coupling sites at one site in the molecule, and a second coupling group for attachment to the protein, polypeptide, label, or other molecule of interest. Numerous bifunctional cross-linkers are well known to those of skill in the art.

Regarding the use of such EDDP analog conjugates, the present invention relates to methods for preparing an antibody. These methods comprise using one or more conjugates as an immunogen to stimulate an immune response.

In certain embodiments, methods may comprise administering one or more conjugates of the invention in a suitable immunization protocol, and separating an appropriate antibody from a body fluid of the animal. Exemplary protocols for preparing immunogens, immunization of animals, and collection of antiserum may be found in ANTIBODIES: A LABORATORY MANUAL, E. Harlow and D. Lane, eds., Cold Spring Harbor Laboratory (Cold Spring Harbor, N.Y., 1988) pp. 55-120, which is hereby incorporated by reference. Alternatively, the EDDP analog conjugates of the present invention may be used in phage display methods to select phage displaying on their surface an appropriate antibody, followed by separation of nucleic acid sequences encoding at least a variable domain region of an appropriate antibody. Phage display methods are well known to those of skill in the art. Such methods may use immunized or unimmunized animals as a source of nucleic acids to form the phage display library. Antibodies prepared in this manner may preferably find use as therapeutic molecules and/or as receptors in receptor binding assays.

Preferably, such antibodies bind EDDP with an affinity that is at least a factor of 5, more preferably at least a factor of 10, still more preferably at least a factor of 30, and most preferably at least a factor of 50 or more, than an affinity for methadone.

Antibodies prepared in this manner may be used as specific binding reagents in immunoassays for determining EDDP concentrations in samples. By way of example, a method can comprise performing a competitive immunoassay in using a conjugate of the present invention in which P is a detectable label, the method comprising determining the concentration of EDDP in the sample from the assay signal. Preferably, immunoassays provide a signal that is at least a factor of 5, more preferably at least a factor of 10, still more preferably at least a factor of 30, and most preferably at least a factor of 50 or more for 10 µg/mL EDDP, compared to the signal obtained from 10 µg/mL, and more preferably 1000 µg/mL, methadone.

Other embodiments of the invention will be apparent from the following detailed description, exemplary embodiments, and claims.

DETAILED DESCRIPTION OF THE INVENTION

Figure 1:
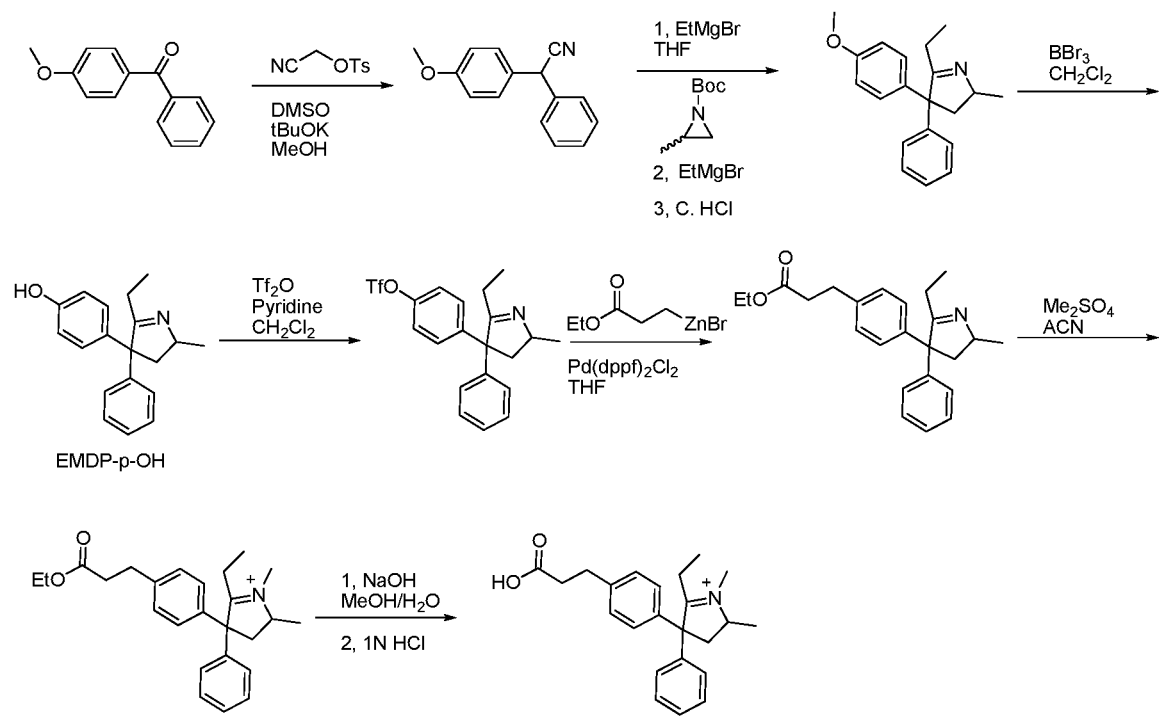
FIG. 1 depicts an exemplary reaction scheme for the synthesis of a carboxyethyl EDDP analog of the invention.

The present invention relates in part to EDDP analogs and methods for their production and use, particularly for preparing cross-linkable EDDP analogs for conjugation to another molecule, and for use of such conjugates for preparing reagents for immunoassays that detect EDDP and in the performance of such immunoassays e.g., as labeled conjugates. The analogs of the present invention are particularly well suited for producing antibodies and labels for use in receptor binding assays for EDDP that can distinguish EDDP from methadone.

For the sake of clarity, definitions for the following terms regarding the compounds of the present invention are provided.

As used herein, the term "aryl" refers to an optionally substituted aromatic group with at least one ring having a conjugated pi-electron system, containing up to two conjugated or fused ring systems. Aryl includes carbocyclic aryl, heterocyclic aryl and biaryl groups, all of which may be optionally substituted. Preferably, the aryl is either optionally substituted phenyl, optionally substituted pyridyl, optionally substituted benzothiopyranyl, optionally substituted carbazole, optionally substituted naphthyl, optionally substituted tetrahydronaphthyl. While "aryl" is most preferably a monocyclic carbocyclic aromatic ring having 5 or 6 ring atoms (and is most preferably phenyl), the aryl or heteroaryl Ar group (formed into an arylene or heteroarylene in the crosslinkers described herein by elaboration from a ring atom) generally may contain up to ten ring atoms, although the skilled artisan will recognize that aryl groups with more than ten ring atoms are within the scope of the invention. The ring systems encompassed by Ar can contain up to four heteroatoms, independently selected from the group consisting of N, S, and O.

Monocyclic aryl groups include, but are not limited to: phenyl, thiazoyl, furyl, pyranyl, 2H-pyrrolyl, thienyl, pyrroyl, imidazoyl, pyrazoyl, pyridyl, pyrazinyl, pyrimidinyl, and pyridazinyl moieties. Fused bicyclic Ar groups include, but are not limited to: benzothiazole, benzimidazole, 3H-indolyl, indolyl, indazoyl, purinyl, quinolizinyl, isoquinolyl, quinolyl, phthalizinyl, naphthyridinyl, quinazolinyl, cinnolinyl, isothiazolyl, quinoxalinyl indolizinyl, isoindolyl, benzothienyl, benzofuranyl, isobenzofuranyl, and chromenyl moieties.

As used herein, the term "heteroatom" refers to non-carbon, non-hydrogen atoms such as N, O, and S.

The aryl group may also be optionally substituted by replacement of one or more hydrogen atoms by another chemical moiety. Preferred substituents include $C_{1-6}$ alkyl straight or branched (e.g. isopropyl) chain, halogen, trihalomethyl, alkoxy, $NO_2$, $NH_2$, OH, —COOR', where R' is H or lower alkyl, $CH_2OH$, and $CONH_2$.

As used herein, the term "alkyl" refers to a saturated aliphatic hydrocarbon including straight chain and branched chain groups. Preferably, the alkyl group has 1 to 20 carbon atoms. More preferably, it is a medium alkyl (having 1 to 10 carbon atoms). Most preferably, it is a lower alkyl (having 1 to 4 carbon atoms). The alkyl group may be substituted or unsubstituted.

As used herein, the term "alkoxy" group refers to both an —O-alkyl and an —O-cycloalkyl group; preferably an alkoxy group refers to a lower alkoxy, and most preferably methoxy or ethoxy.

As used herein, the term "thiolactone" refers to a cyclic hydrocarbon having 5 or 6 ring atoms, one of which is an S heteroatom, and where the heteroatom is adjacent to a carbon substituted with a =O.

As used herein, the term "thioester" refers to an organic compound having the structure R—S—C(O)—R'.

As used herein, the term "alkyl thiol" refers to an alkyl group containing an —SH group. Thiols are also referred to as "thio alcohols" and "sulfhydryls."

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

The term "polypeptide" as used herein refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the invention, treated as a subclass of the polypeptides and derivatives. The term protein refers to a polypeptide that is isolated from a natural source, or produced from an isolated cDNA using recombinant DNA technology, and that has a sequence of amino acids having a length of at least about 200 amino acids.

The term "nucleic acids" as used herein shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of purine or pyrimidine bases, or modified purine or pyrimidine bases.

The term "aptamer" as used herein is a single-stranded or double-stranded oligodeoxyribonucleotide, oligoribonucleotide or modified derivatives that specifically bind and alter the biological function of a target molecule. The target molecule is defined as a protein, peptide and derivatives thereof. The aptamer is capable of binding the target molecule under physiological conditions. An aptamer effect is distinguished from an antisense effect in that the aptameric effects are induced by binding to the protein, peptide and derivative thereof and are not induced by interaction or binding under physiological conditions with nucleic acid.

The term "polysaccharide" as used herein refers to a molecule comprising more than 10 glycosidically linked monosaccharide residues, while the term "oligosaccharide" refers to a molecule comprising from 2-10 glycosidically linked monosaccharide residues.

The term "small molecule" includes any molecule having a molecular weight less than about 5,000 daltons (Da), preferably less than about 2,500 Da, more preferably less than 1,000 Da, most preferably less than about 500 Da.

Functional Moieties

Chemical cross-linkers are valuable tools for preparing antibody-detectable label conjugates, immunotoxins and other labeled protein and nucleic acid reagents. These reagents may be classified on the basis of the following:

1. Functional groups and chemical specificity;
2. length and composition of the cross-bridge;
3. whether the cross-linking groups are similar (homobifunctional) or different (heterobifunctional);
4. whether the groups react chemically or photochemically;
5. whether the reagent is cleavable; and
6. whether the reagent can be radiolabeled or tagged with another label.

As the compounds of the present invention provide an available thiol to act as an attachment point, targets may be prepared to provide an appropriate thiol-reactive site. Cross-linking reagents that couple through sulfhydryls (thiols) are available from many commercial sources. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Such reagents may be bifunctional, in that a second site on the reagent is available for use in modifying a conjugation target to incorporate the thiol-reactive site. In addition to thiols, reactive groups that can be targeted using a cross-linker include primary amines, carbonyls, carbohydrates and carboxylic acids. In addition, many reactive groups can be coupled nonselectively using a cross-linker such as photoreactive phenyl azides. Thus, a two-step strategy allows for the coupling of a protein that can tolerate the modification of its amines to a EDDP analog of the invention. For suitable reagents, see Pierce 2003-2004 Applications Handbook and Catalog #1600926, which is hereby incorporated by reference. Cross-linkers that are amine-reactive at one end and sulfhydryl-reactive at the other end are quite common. If using heterobifunctional reagents, the most labile group is typically reacted first to ensure effective cross-linking and avoid unwanted polymerization.

Many factors must be considered to determine optimum cross-linker-to-target molar ratios. Depending on the application, the degree of conjugation is an important factor. For example, when preparing immunogen conjugates, a high degree of conjugation is normally desired to increase the immunogenicity of the antigen. However, when conjugating to an antibody or an enzyme, a low-to-moderate degree of conjugation may be optimal to ensure that the biological activity of the protein is retained. It is also important to consider the number of reactive groups on the surface of the protein. If there are numerous target groups, a lower cross-linker-to-protein ratio can be used. For a limited number of potential targets, a higher cross-linker-to-protein ratio may be required. This translates into more cross-linker per gram for a small molecular weight protein.

Conformational changes of proteins associated with a particular interaction may also be analyzed by performing cross-linking studies before and after the interaction. A comparison is made by using different arm-length cross-linkers and analyzing the success of conjugation. The use of cross-linkers with different reactive groups and/or spacer arms may be desirable when the conformation of the protein changes such that hindered amino acids become available for cross-linking.

Cross-linkers are available with varying lengths of spacer arms or bridges connecting the reactive ends. The most apparent attribute of the bridge is its ability to deal with steric considerations of the moieties to be linked. Because steric effects dictate the distance between potential reaction sites for cross-linking, different lengths of bridges may be considered for the interaction. Shorter spacer arms are often used in intramolecular cross-linking studies, while intermolecular cross-linking is favored with a cross-linker containing a longer spacer arm.

The inclusion of polymer portions (e.g., polyethylene glycol ("PEG") homopolymers, polypropylene glycol homopolymers, other alkyl-polyethylene oxides, bis-polyethylene oxides and co-polymers or block co-polymers of poly(alkylene oxides)) in cross-linkers can, under certain circumstances be advantageous. See, e.g., U.S. Pat. Nos. 5,643,575, 5,672,662, 5,705,153, 5,730,990, 5,902,588, and 5,932,462; and Topchieva et al., Bioconjug. Chem. 6: 380-8, 1995). For example, U.S. Pat. No. 5,672,662 discloses bifunctional cross-linkers comprising a PEG polymer portion and a single ester linkage. Such molecules are said to provide a half-life of about 10 to 25 minutes in water.

Designing a cross-linker involves selection of the functional moieties to be employed. The choice of functional moieties is entirely dependent upon the target sites available on the species to be crosslinked. Some species (e.g., proteins) may present a number of available sites for targeting (e.g., lysine ε-amino groups, cysteine sulfhydryl groups, glutamic acid carboxyl groups, etc.), and selection of a particular functional moiety may be made empirically in order to best preserve a biological property of interest (e.g., binding affinity of an antibody, catalytic activity of an enzyme, etc.)

1. Coupling Through Amine Groups

Imidoester and N-hydroxysuccinimidyl ("NHS") esters are typically employed as amine-specific functional moieties. NHS esters yield stable products upon reaction with primary or secondary amines. Coupling is efficient at physiological pH, and NHS-ester cross-linkers are more stable in solution than their imidate counterparts. Homobifunctional NHS-ester conjugations are commonly used to cross-link amine-containing proteins in either one-step or two-step reactions. Primary amines are the principle targets for NHS-esters. Accessible α-amine groups present on the N-termini of proteins react with NHS-esters to form amides. However, because α-amines on a protein are not always available, the reaction with side chains of amino acids become important. While five amino acids have nitrogen in their side chains, only the ε-amino group of lysine reacts significantly with NHS-esters. A covalent amide bond is formed when the NHS-ester cross-linking agent reacts with primary amines, releasing N-hydroxysuccinimide.

2. Coupling through Sulfhydryl Groups

Maleimides, alkyl and aryl halides, α-haloacyls, and pyridyl disulfides are typically employed as sulfhydryl-specific functional moieties. The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not react with tyrosines, histidines or methionines. When free sulfhydryls are not present in sufficient quantities, they can often be generated by reduction of available disulfide bonds.

3. Coupling Through Carboxyl Groups

Carbodiimides couple carboxyls to primary amines or hydrazides, resulting in formation of amide or hydrazone bonds. Carbodiimides are unlike other conjugation reactions in that no cross-bridge is formed between the carbodiimide and the molecules being coupled; rather, a peptide bond is formed between an available carboxyl group and an available amine group. Carboxy termini of proteins can be targeted, as well as glutamic and aspartic acid side chains. In the presence of excess cross-linker, polymerization may occur because proteins contain both carboxyls and amines. No cross-bridge is formed, and the amide bond is the same as a peptide bond, so reversal of the cross-linking is impossible without destruction of the protein.

4. Nonselective Labeling

A photoaffinity reagent is a compound that is chemically inert but becomes reactive when exposed to ultraviolet or visible light. Arylazides are photoaffinity reagents that are photolyzed at wavelengths between 250-460 nm, forming a reactive aryl nitrene. The aryl nitrene reacts nonselectively to form a covalent bond. Reducing agents must be used with caution because they can reduce the azido group.

5. Carbonyl Specific Cross-Linkers

Carbonyls (aldehydes and ketones) react with amines and hydrazides at pH 5-7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones.

Exemplary Applications for Use of Cross-Linkable EDDP Analogs

1. Carrier Protein-Hapten/Peptide/Polypeptide Conjugates for Use as Immunogens

Numerous companies offer commercially available products in this area of immunological research. There are many cross-linkers used for the production of these conjugates, and the best choice is dependent on the reactive groups present on the hapten and the ability of the hapten-carrier conjugate to function successfully as an immunogen after its injection. Carbodiimides are good choices for producing peptide carrier conjugates because both proteins and peptides usually contain several carboxyls and primary amines. Other cross-linkers can also be used to make immunogen conjugates.

Adjuvants are mixtures of natural or synthetic compounds that, when administered with antigens, enhance the immune response. Adjuvants are used to (1) stimulate an immune response to an antigen that is not inherently immunogenic, (2) increase the intensity of the immune response, (3) preferentially stimulate either a cellular or a humoral response (i.e., protection from disease versus antibody production). Adjuvants have four main modes of action: enhanced antigen uptake and localization, extended antigen release, macrophage activation, and T and B cell stimulation. The most commonly used adjuvants fall into six categories: mineral salts, oil emulsions, microbacterial products, saponins, synthetic products and cytokines. A more extensive discussion of adjuvants and their use in immunization protocols is given in IMMUNOLOGY METHODS MANUAL, vol. 2, I. Lefkovits, ed., Academic Press, San Diego, Calif., 1997, ch. 13, which is hereby incorporated in its entirety Small molecules such as EDDP are not usually immunogenic, even when administered in the presence of adjuvant. In order to generate an immune response to these compounds, it is often necessary to attach them to a protein or other compound, termed a carrier, that is immunogenic. When attached to a carrier protein the small molecule immunogen is called a hapten. Haptens are also conjugated to carrier proteins for use in immunoassays. The carrier protein provides a means of attaching the hapten to a solid support such as a microtiter plate or nitrocellulose membrane. When attached to agarose they may be used for purification of the anti-hapten antibodies. They may also be used to create a multivalent antigen that will be able to form large antigen-antibody complexes. When choosing carrier proteins, remember that the animal will form antibodies to the carrier protein as well as to the attached hapten. It is therefore important to select a carrier protein for immunization that is unrelated to proteins that may be found in the assay sample. If haptens are being conjugated for both immunization and assay, the two carrier proteins should be as different as possible. This allows the antiserum to be used without having to isolate the anti-hapten antibodies from the anti-carrier antibodies.

Keyhole limpet hemocyanin (KLH) is a respiratory protein found in mollusks. Its large size makes it very immunogenic, and the large number of lysine residues available for conjugation make it very useful as a carrier for haptens such as EDDP. The phylogenic separation between mammals and mollusks increases the immunogenicity and reduces the risk of cross-reactivity between antibodies against the KLH carrier and naturally occurring proteins in mammalian samples.

2. Solid-Phase Immobilization

The analogs and/or conjugates of the present invention can be immobilized on solid-phase matrices for use as affinity supports or for sample analysis. Similarly, antibodies or their binding fragments made or selected using the EDDP analogs and/or conjugates of the present invention can also be immobilized on solid-phase matrices. The term "solid phase" as used herein refers to a wide variety of materials including solids, semi-solids, gels, films, membranes, meshes, felts, composites, particles, papers and the like typically used by those of skill in the art to sequester molecules. The solid phase can be non-porous or porous. Suitable solid phases include those developed and/or used as solid phases in solid phase binding assays. See, e.g., chapter 9 of *Immunoassay*, E. P. Dianiandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997, 1998; Kessler et al., Agnew. Chem. Int. Ed. 40: 165, 2001; Smith et al., J. Comb. Med. 1: 326, 1999; Orain et al., Tetrahedron Lett. 42: 515, 2001; Papanikos et al., J. Am. Chem. Soc. 123: 2176, 2001; Gottschling et al., Bioorg. Med. Chem. Lett. 11: 2997, 2001.

Surfaces such as those described above may be modified to provide linkage sites, for example by bromoacetylation, silation, addition of amino groups using nitric acid, and attachment of intermediary proteins, dendrimers and/or star polymers. This list is not meant to be limiting, and any method known to those of skill in the art may be employed.

3. Detectable Label Conjugates

Biological assays require methods for detection, and one of the most common methods for quantitation of results is to conjugate an enzyme, fluorophore or other detectable label to the molecule under study (e.g., using one or more analogs of the invention), which may be immobilized for detection by a receptor molecule that has affinity for the molecule. Alternatively, the receptor to the molecule under study (e.g., an antibody or binding fragment thereof made or selected using the analogs or conjugates of the invention) may be conjugated to an enzyme, fluorophore or other detectable label. Enzyme conjugates are among the most common conjugates used. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Particularly preferred detectable labels are fluorescent latex particles such as those described in U.S. Pat. Nos. 5,763,189, 6,238,931, and 6,251,687; and International Publication WO95/08772, each of which is hereby incorporated by reference in its entirety. Exemplary conjugation to such particles is described hereinafter.

Use of EDDP Analogs in Receptor Binding Assays

EDDP analogs and conjugates of the present invention may be advantageously used in receptor binding assays. Receptor binding assays include any assay in which a signal is dependent upon specific binding of an analyte to a cognate receptor, and include immunoassays, ligand-receptor assays, and nucleic acid hybridization assays.

The presence or amount of an analyte is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

Numerous methods and devices are well known to the skilled artisan for the practice of receptor binding assays. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize detectably labeled molecules and antibody solid phases in various sandwich, competitive, or non-competitive assay formats, to generate a signal that is related to the presence or amount of an analyte of interest. One skilled in the art also recognizes that robotic instrumentation including but not limited to Beckman Access, Abbott AxSym, Roche ElecSys, Dade Behring Stratus systems are among the immunoassay analyzers that are capable of performing such immunoassays. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. As described herein, preferred assays utilize an antibody raised against an analog conjugate (wherein the antibody is coupled to a solid phase or a detectable label), and/or a EDDP analog conjugated to a detectable label, and/or a EDDP analog conjugated to a solid phase.

In its simplest form, an assay device according to the invention may comprise a solid surface comprising receptor(s) that specifically bind one or more analytes of interest (e.g., EDDP). For example, antibodies may be immobilized onto a variety of solid supports, such as magnetic or chromatographic matrix particles, the surface of an assay plate (such as microtiter wells), pieces of a solid substrate material or membrane (such as plastic, nylon, paper), and the like using the cross-linkers of the present invention. In similar fashion, an assay device may comprise a solid surface comprising one or more of the EDDP analogs described herein immobilized thereon.

The analysis of a plurality of analytes may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of analytes on a single surface. Particularly useful physical formats comprise surfaces having a plurality of discrete, addressable locations for the detection of a plurality of different analytes. Such formats include protein microarrays, or "protein chips" (see, e.g., Ng and Ilag, *J. Cell Mol. Med.* 6: 329-340 (2002)) and certain capillary devices (see, e.g., U.S. Pat. No. 6,019,944). In these embodiments, each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

EXEMPLARY EMBODIMENTS

Embodiment 1

A compound or salt thereof, said compound having a general formula selected from (I), (II), (III), (IV), or (V):

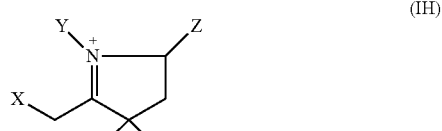

(IH)

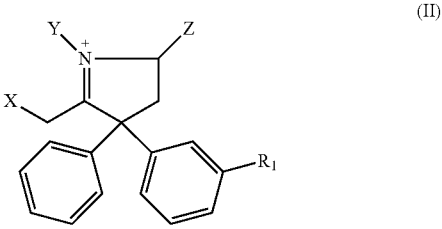

(II)

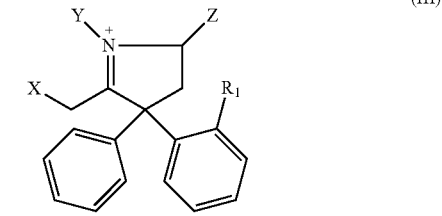

(III)

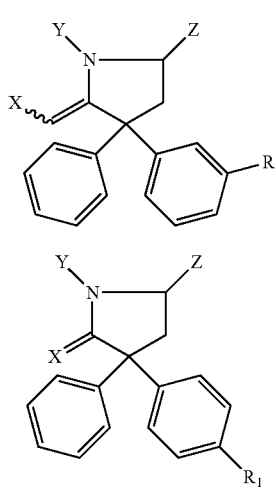

(IV)

(V)

wherein R and R1 are each —CH$_2$—R2, where R2 is a linkage chemistry which provides a terminal functional moiety selected from the group consisting of protected or unprotected sulfhydryl moieties, protected or unprotected amine moieties, primary amine-reactive moieties, sulfhydryl-reactive moieties, photoreactive moieties, carboxyl-reactive moieties, arginine-reactive moieties, and carbonyl-reactive moieties;

X is H, N, O, C$_{1-6}$ saturated alkyl straight or branched chain, C$_{1-6}$ unsaturated alkyl straight or branched chain, C$_{1-6}$ alkoxy, or haloalkyl;

Y is H, C$_{1-6}$ saturated alkyl straight or branched chain, C$_{1-6}$ unsaturated alkyl straight or branched chain, C$_{1-6}$ alkoxy, or haloalkyl;

Z is H, C$_{1-6}$ saturated alkyl straight or branched chain, C$_{1-6}$ unsaturated alkyl straight or branched chain, C$_{1-6}$ alkoxy, or haloalkyl.

Embodiment 2

A compound or salt thereof according to embodiment 1, wherein R2 is —(CH$_2$)$_n$R3, wherein n is 0 to 6 and R3 is a functional moiety selected from the group consisting of protected or unprotected sulfhydryl moieties, protected or unprotected amine moieties, primary amine-reactive moieties, sulfhydryl-reactive moieties, photoreactive moieties, carboxyl-reactive moieties, arginine-reactive moieties, and carbonyl-reactive moieties.

Embodiment 3

A compound or salt thereof according to embodiment 1 or 2, wherein the functional moiety is selected from the group consisting of a maleimide, an alkyl halide, an aryl halide, an alpha-haloacyl, an activated aryl, a pyridyl disulfide, a carbonyl, a carboxyl, a thiol, a thioester, disulfide, or a cyclic thiolactone.

Embodiment 4

A compound or salt thereof according to embodiment 3, wherein R2 is —(CH$_2$)$_{1-4}$—S—C(O)—CH$_3$, —(CH$_2$)$_{1-4}$—C(O)—OH, —(OCH2CH2)n-R3 where n is between 0 and 25, or Embodiment 5

A compound or salt thereof according to embodiment 3, wherein the compound is selected from the group consisting of

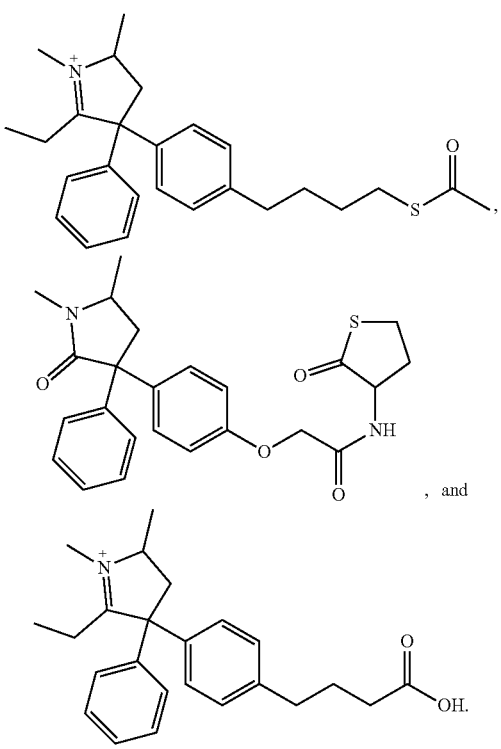

Embodiment 6

A conjugate comprising one or more compounds according to one of embodiments 1-5 covalently bound through the functional moiety on the compound(s) to a corresponding coupling site on a protein, polypeptide, detectable label, nucleic acid, or solid phase.

Embodiment 7

A conjugate according to embodiment 6, wherein the functional moiety is a sulfhydryl-reactive moiety.

Embodiment 8

A conjugate according to embodiment 7, wherein said sulfhydryl-reactive moiety is a maleimide.

Embodiment 9

A conjugate according to embodiment 7, wherein said sulfhydryl-reactive moiety is an alkyl halide, an aryl halide, an acryl, or an α-haloacyl, wherein the sulfhydryl-reactive moiety reacts with sulfhydryls to form thiol ether bonds.

Embodiment 10

A conjugate according to embodiment 6, wherein the functional moiety is a carbonyl-reactive moiety.

Embodiment 11

A conjugate according to one of embodiments 6-10, wherein said detectable label is selected from the group consisting of an enzyme, a fluorophore, biotin, avidin, streptavidin, digoxigenin, maltose, oligohistidine, 2,4-dintrobenzene, phenylarsenate, a metal, a fluorescent or colored microsphere, and a fluorescent or colored latex particle.

Embodiment 12

A conjugate according to according to one of embodiments 6-10, wherein said protein is keyhole limpet hemocyanin, bovine serum albumin, thyroglobulin, ovalbumin, lysozyme, or dextran.

Embodiment 13

A conjugate according to one of embodiments 6-10, wherein said compound(s) are bound to a solid phase selected from the group consisting of a membrane, a cellulose-based paper, a polymeric particle, a latex particle, a paramagnetic particle, a gold particle, a magnetic particle, a metallic particle, a plasmonic particle, a glass substrate, a silicon substrate, a plastic substrate, and a multiple-well plate.

Embodiment 14

A method of preparing a conjugate, comprising:
contacting one or more compounds of one of embodiments 1-5 with a protein, polypeptide, detectable label, nucleic acid, or solid phase under conditions to provide covalent coupling of said compound(s) to said protein, polypeptide, detectable label, nucleic acid, or solid phase through a reactive moiety on the compound(s).

Embodiment 15

A method according to claim 14, wherein said compound(s) comprise a protected reactive moiety, and said method further comprises deprotecting said reactive moiety following, or together with, said contacting step.

Embodiment 16

A method according to embodiment 14 or 15, wherein said method further comprises introducing said one or more coupling sites corresponding to the reactive moiety into said protein, polypeptide, detectable label, nucleic acid, or solid phase prior to said contacting step.

Embodiment 17

A method according to embodiment 16, wherein said reactive moiety is a sulfhydryl-reactive moiety, and said introducing step comprises coupling of said protein, polypeptide, detectable label, nucleic acid, or solid phase to one or more bivalent crosslinkers comprising said one or more sulfhydryl-reactive moieties.

Embodiment 18

A method of stimulating an immune response to EDDP, comprising:
immunizing an animal with a conjugate of one of embodiments 6-13.

Embodiment 19

A method according to embodiment 18, further comprising isolating one or more antibodies that specifically bind EDDP.

Embodiment 20

A method according to embodiment 19, wherein said one or more antibodies are isolated directly from said animal.

Embodiment 21

A method of determining an EDDP concentration in a sample, comprising:
performing a competitive binding assay using a conjugate according to one of embodiments 6-11 which competes with EDDP in said sample for binding to an antibody, wherein the conjugate comprises a detectable label covalently bound thereto, wherein a signal obtained from determining an amount of detectable label bound to the antibody in said assay is indicative of the concentration of EDDP in said sample; and
determining the concentration of EDDP in said sample from the assay signal.

EXAMPLES

The following examples serve to illustrate the present invention. These examples are in no way intended to limit the scope of the invention.

Example 1: General Methods

All starting materials and solvents were obtained from commercial vendors unless otherwise noted. 1H NMR spectra were taken in DMSO D6 (from ampoules) or CDCl3 at 500 MHz by NuMega Laboratories. HPLC was conducted using an Agilent Model 1200 machine equipped with either a Waters X-bridge (C18, 3.5 µm, 3.0×50 µm) or Fisher Thermo Hypercarb (5.0 um, 4.6×100 mm) columns. For HPLC, solvent A was 95% H2O/5% CH3CN/0.1% TFA, solvent B was 95% CH3CN/5% H2O/0.1% TFA. HPLC runs were either 6 or 15 minutes long. For the 6 minute run: 0 minutes, 5% B, 0-5 minutes, gradient to 100% B, 5-6 minutes, gradient to 5% B; for the 15 minute run: 0 minutes 0% B, 0-12 minutes, gradient to 100% B, 12-14 minutes 100% B, 14-15 minutes, gradient to 0% B. LC/MS was conducted using a Waters model e2795 series LC equipped with a model 2996 photodiode array detector, a series 3100 MS and a Waters X-Bridge-C18 column, 3.5 um, 2.1×50 mm. For LC/MS, solvent A was 95% H2O/5% CH3CN/ 0.1% Formic Acid; solvent B was 95% CH3CN/5% H2O/ 0.1% Formic Acid. HPLC runs were 5 minutes: 0 minutes 0% B, 0-3.5 minutes, gradient to 100% B, 3.5-4.8 minutes 100% B, 4.8 to 4.9 minutes gradient to 0% B, 5.0 minutes, 0% B.

Example 2: Compound I

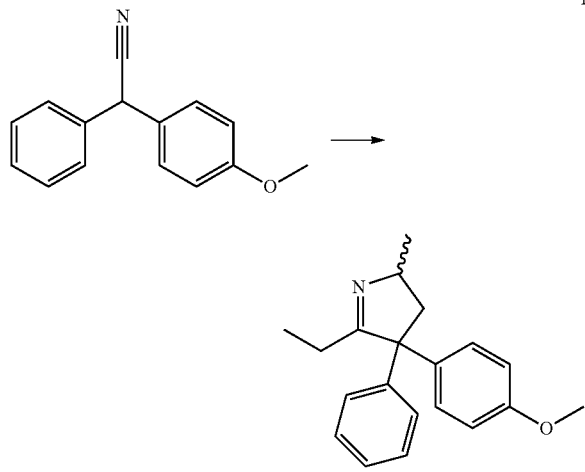

2-(4-methoxyphenyl)-2-phenylacetonitrile (8.96 mmol) was placed in a 100 mL RB flask containing a stir bar. Ethyl Grignard (9.85 mmol) was added in a drop-wise fashion to the neat nitrile and stirred at room temperature for 45 minutes. The tert-butyl-2-methyl aziridine (9.85 mmol) was added neat at RT to the crude reaction. The resulting solution was stirred at room temperature for 1.5 hours. After this time period, additional ethyl grignard (35.8 mmol) was added then incubated overnight at room temperature. The crude reaction was poured slowly into a beaker full of ice. Once the bubbling was controlled the suspension was quenched using 6 M HCl (6 mL) and stirred at room temperature for 30 minutes. The resulting mixture was transferred into a round bottomed flask. The beaker was rinsed using methanol and combined with the crude which was subsequently concentrated to dryness to afford a sticky oil.

The oil was re-suspended in Dioxane (16 mL) to which was added concentrated HCl (18 mL). A reflux condenser was attached and the mixture stirred at 100 C for 90 minutes. The crude mixture was cooled to room temperature and the dioxane removed in vacuo. The aqueous solution was washed with ethyl acetate (2×40 mL). The pH of the aqueous phase was adjusted to 8 using solid NaOH then transferred to a separatory funnel and extracted using ethyl acetate (3×40 mL). The pooled ethyl acetate was washed with water (40 mL), dried using $Na_2SO_4$, concentrated to dryness, then purified via silica gel chromatography. Yield=69%. TLC: Rf=0.33, 30% Ethyl Acetate/Hexanes. LC/MS 294 (M+). NMR (DMSO-d6): 7.31-7.35 (q, J=16.5 Hz, 2H), 7.2-7.28 (m, 1H), 7.08-7.10 (m, 2H), 7.01 (dd, $J_1$=17.7 Hz, $J_2$=24.5 Hz, 2H), 6.89-6.92 (m, 2H), 3.74 (d, J=12 Hz, 3H), 2.60-2.68 (m, 1H), 1.90-2.13 (m, 3H), 1.27 (d, J=13.5 Hz, 3H).

Example 3: Compound II

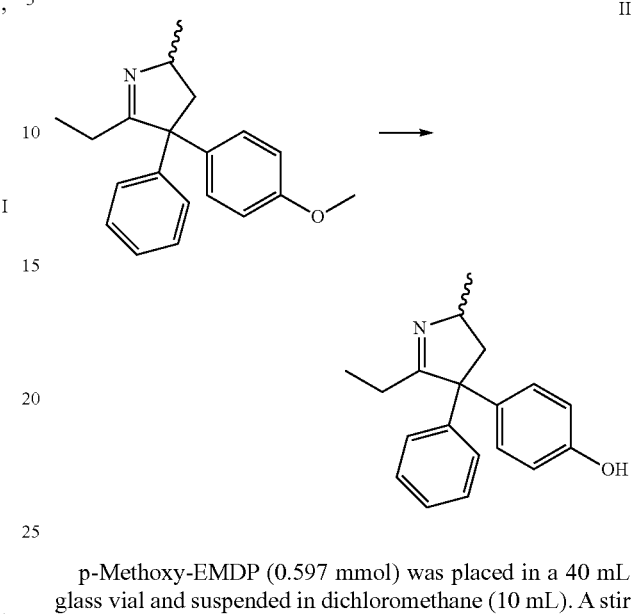

p-Methoxy-EMDP (0.597 mmol) was placed in a 40 mL glass vial and suspended in dichloromethane (10 mL). A stir bar was added to the vial and subsequently sealed using a teflon lined cap and placed under argon. The reaction was stirred and cooled using an ice bath. Tribromoborane (1.19 mmol, 1 M in DCM) was added and the reaction warmed to room temperature then stirred at room temperature for 14 hours. After this time period, methanol (3 mL) was added and the reaction stirred for an additional 1 hour. The solvents were evaporated to give a dark oil that was partitioned in a separatory funnel between dichloromethane (50 mL) and saturated $NaHCO_3$ (30 mL). The aqueous layer was separated then washed using dichloromethane (30 mL). The organic extracts were combined and washed with water (15 mL), dried using $Na_2SO_4$, and concentrated, Purification via silica gel chromatography yielded an off-white foam. Yield=99%. TLC: 30% EA/HEX, Rf=0.22 (diastereomers visible). LC/MS 295 (M+H+). $^1$H NMR (500 MHz, DMSO $D_6$) δ 9.38 (bs, OH), 7.33 (q, J=16.8 Hz, 2H), 7.24 (quint, J=12.6 Hz, 1H), 7.08 (m, 2H), 6.89 (dd, $J_1$=13 Hz, $J_2$=9.5 Hz, 2H), 6.72 (m, 2H), 3.70-3.76 (m, 1H), 2.56-2.66 (m, 1H), 1.90-2.11 (m, 3H), 1.26 (d, J=13 Hz, 3H), 0.99 (m, 3H).

Example 4: Compound III

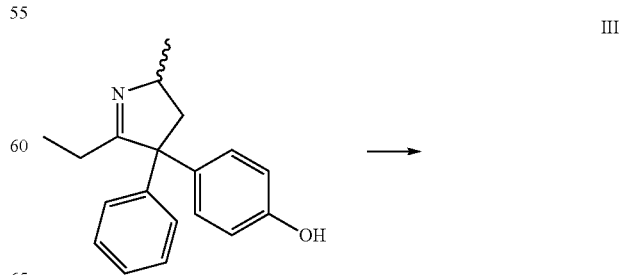

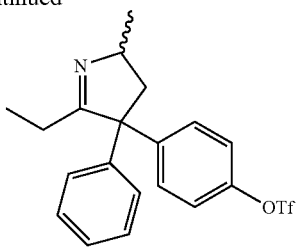

p-hydroxy EMDP phenol (0.794 mmol) was placed in a glass vial containing a stir bar. To the vial were added 15 mL of dichloromethane followed by 0.5 mL of methanol and gently stirred. Once the material was homogenous, 1 M HCl in ether (3.97 mmol) was added and the reaction purged with argon then capped and stirred at RT. After 20 min the solution was concentrated in vacuo to remove all volatiles then placed under high vacuum for 30 min. 10 mL of DCM were added to the light yellow oil and the solution was concentrated once again and placed under high vacuum for 30 min.

The resulting HCl salt (0.794 mmol) was dissolved in dichloroethane (16 mL). The solution was placed under argon, sealed using a Teflon lined cap, and stirred at room temperature until homogenous. Trifluoromethanesulfonic anhydride (Triflic anhydride) (7.94 mmol) was acclimated to room temperature and added to the mixture. The reaction temperature was adjusted (80° C.) and maintained overnight. The crude reaction was cooled using an ice bath and stirred (10 min). The ice bath was removed upon addition of methanol (2 mL) and the reaction stirred at room temperature (10 min). The solvents were evaporated and the dark oil was partitioned in a separatory funnel between dichloromethane (50 mL) and saturated $NaHCO_3$ (20 mL). The aqueous layer was collected and back extracted with dichloromethane (20 mL). The organic extracts were combined then washed with water (15 mL), dried using $Na_2SO_4$, concentrated, and purified via silica gel chromatography. Product isolated as a light yellow oil. Isolated Yield=83%. TLC: 30% EA/HEX, Rf=0.32. LC/MS: 412 (M+H$^+$).

Example 5: Compound IV

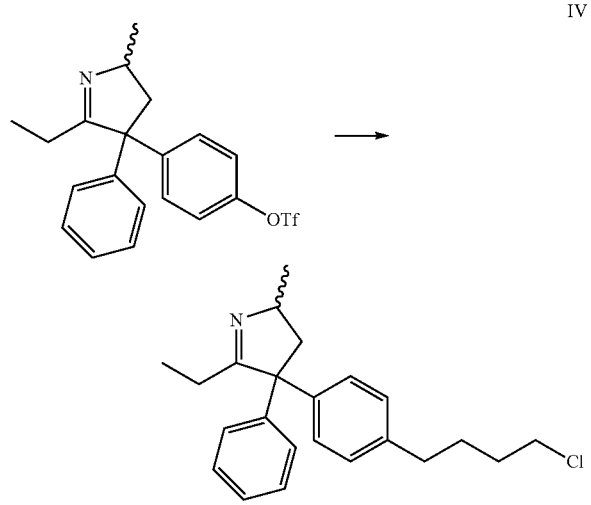

p-Hydroxy EMDP aryl triflate (0.636 mmol) was dissolved in anhydrous THF (7 mL) and sparged with argon. The vessel was sealed and stirred under argon for 10 minutes after which bromo-4-(chlorobutyl)zinc (3.82 mmol) was added. Pd(dppf)$_2$Cl$_2$-DCM complex (0.064 mmol) was added quickly as a solid. The reaction was stirred at reflux under argon for 4 hours at which time the solvents were evaporated to yield a dark oil. The residue was purified via silica gel column chromatography giving a pale yellow oil after evaporation. The product contained a small amount of inconsequential impurities. Isolated yield=102% yield. TLC: Rf=0.4 in 30% EA/Hex. $^1$H NMR (500 MHz, DMSO D$_6$) δ 7.29-7.41 (m, 3H), 7.09-7.24 (m, 5H), 7.04 (d, J=16 Hz, 1H), 3.65 (q, J=9 Hz, 2H), 2.60 (q, J=15 Hz, 2H), 2.22 (bm, 3H), 1.65-1.76 (m, 4H), 1.33 (d, J=17 Hz, 3H), 0.99 (t, J=15 Hz, 3H). LC/MS: 355 (M+H$^+$).

Example 6: Compound V

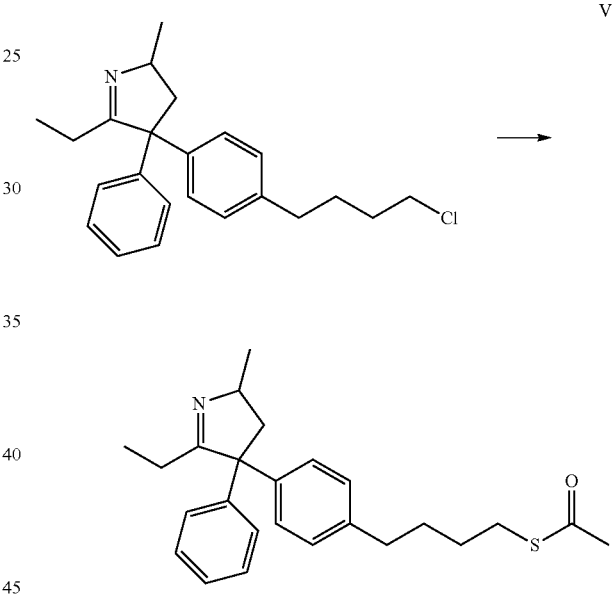

p-Chlorobutyl-EMDP # (0.466 mmol) was taken up in glass vial containing a stir bar. Potassium thioacetate (4.6 mmol) was weighed and added to the vial as a solid. Anhydrous ACN (6 mL) was added and the solution purged with argon then sealed with a Teflon lined cap. The resulting solution was heated at 75° C. for 6 hours at which time the black colored reaction was diluted with acetonitrile (10 mL) then filtered using a pad of celite to remove the solids. The flask and the celite were washed extensively using acetonitrile (20 mL) and the collected filtrate concentrated and subsequently purified via column chromatography. Isolated yield (2 steps)=77%. TLC: Rf=0.14 in 10% EA/Hexane. NMR (DMSO-d$_6$): 7.31-7.37 (m, 2H), 7.24 (m, 1H), 7.14-7.18 (m, 2H), 7.07-7.11 (m, 2H), 6.98-7.02 (m, 2H), 3.76-3.82 (m, 1H), 2.84-2.88 (m, 2H), 2.64-2.69 (m, 1H), 2.56 (q, 2H), 2.31 (s, 3H), 1.98-2.14 (m, 2H), 1.86-1.95 (m, 1H), 1.49-1.65 (m, 4H), 1.26 (dd, 3H), 0.97 (t, 3H).

Example 7: Compound VI

VI

Desmethyl-p-pentylthioacetate # (0.485 mmol) was dissolved in anhydrous ACN (10 mL) and magnetically stirred. To the homogenous mixture was added dimethyl sulfate (4.85 mmol). The flask was sealed using a rubber septum, purged with argon, and stirred at RT overnight. The following morning the crude reaction was concentrated to remove the volatile materials. The oil was re-dissolved in ACN (5 mL) and aqueous 1 M HCl (5 mL) added to the solution then stirred for 10 min. The solution was concentrated in vacuo to dryness and then purified via reverse phase column chromatography. Yield=69%. TLC: Rf=0.06, 7% MeOH/DCM. LC/MS 409 (M+). NMR (DMSO-d6): 7.45-7.47 (m, 3H), 7.27-7.29 (m, 3H), 7.20-7.21 (m, 2H), 7.13 (d, 1H), 4.6 (m, 1H), 3.63 (d, 3H), 3.37 (s, 2H), 3.18-3.25 (M, 1H), 2.65-2.87 (m, 4H), 2.62 (t, 2H), 2.31 (t, 3H), 1.62 (quint, 2H), 1.52 (quint, 2H), 1.44 (t, 3H), 0.56 (t, 3H).

Example 8: Compound VII

VII

The reaction was conducted in the same manner as Example 5. Isolated yield=100%. TLC: Rf=0.7 in 5% MeOH/CH$_2$Cl$_2$. $^1$H NMR (500 MHZ, DMSO-d6) δ: 7.32-737 (m, 2H), 7.25 (quint, J=14.7 Hz, 1H), 7.16 (q, J=16.4 Hz, 2H), 7.09 (t, J=15.3 Hz, 2H), 7.01 (q, J$_1$=16.4 Hz, J$_2$=8.1 Hz, 2H), 4.03 (q, J=14.1 Hz, 2H), 3.76-3.78 (m, 1H), 3.32 (s, 3H), 2.63-2.71 (m, 1H), 2.56 (q, J=13.4 Hz, 2H), 3.29 (q, J=14 Hz, 2H), 1.91-2.23 (m, 3H), 1.81 (sept, J=14.4 Hz, 2H), 1.27 (dd, J$_1$=13.5 Hz, J$_2$=3.6 Hz, 3H), 1.17 (t, J=14.2 Hz, 3H), 0.97 (t, J=14.7, 3H). LC/MS: 378 (M+H$^+$).

Example 9: Compound VIII

VIII

Desmethyl-p-pentylthioacetate (0.485 mmol) was dissolved in anhydrous ACN (10 mL) and magnetically stirred. To the homogenous mixture was added dimethyl sulfate (4.85 mmol). The flask was sealed using a rubber septum, purged with argon, and stirred at RT overnight. The following morning the crude reaction was concentrated to remove the volatile materials. The oil was re-dissolved in ACN (5 mL). Aqueous 1 M HCl (5 mL) was added to the solution and stirred for 10 min. The resulting solution was concentrated in vacuo to dryness then purified via reverse phase column chromatography. Isolated Yield=69%. TLC: Rf=0.06, 7% MeOH/DCM. LC/MS: 393 (M$^+$).

Example 10: Compound IX

IX

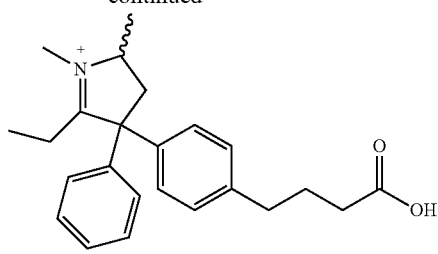

p-EDDP ethylbutyrate # (0.166 mmol) was dissolved in ethanol (5 mL) and water (2.5 mL). To the mixture was added 1 N sodium hydroxide (1 mL) and stirred overnight. The methanol was removed in vacuo and the remaining aqueous mixture acidified using 1 N HCl. The suspension was concentrated to dryness and the solids suspended in acetonitrile (10 mL). The solids were removed by filtration then repeatedly washed using acetonitrile (5 mL). The combined filtrates were evaporated to dryness providing a pink oil. The crude material required no further purification. Isolated Yield=77%. TLC: Rf=0.48 in 10:2:1 IPA/NH$_3$/H$_2$O. NMR (DMSO-d$_6$): δ 7.41-7.47 (m, 3H), 7.27-7.30 (m, 3H), 7.22 (d, J=16.9 Hz, 2H), 7.14 (d, J=16.6 Hz, 1H), 4.60 (sept, J=14.3 Hz, 1H), 3.63 (d, J=5.4 Hz, 3H), 3.19-3.29 (m, 1H), 2.75-2.78 (m, 2H), 2.62 (t, J=14 Hz, 2H), 2.47-2.52 (m, 1H), 2.22 (m, 2H), 1.80 (quint, J=15 Hz, 2H), 1.45 (t, J=14.1 Hz, 3H), 0.56 (m, 3H). LC/MS: 364 (M$^+$).

Example 11: Compound X

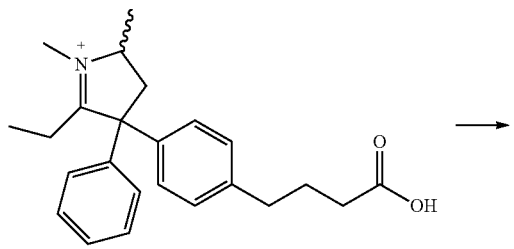

EDDP p-butyric acid # (0.0058 mmol) was dissolved in anhydrous DMF (1 mL). EDAC (0.0174 mmol) and N-hydroxysuccinimide (0.0064 mmol) were added successively and stirred at room temperature under argon for 4 hours. The reaction progress was monitored via LCMS. The indicated amounts of EDAC and N-hydroxysuccinimide were added as necessary until the LCMS indicated a complete reaction. The NHS-p-butyric-EDDP ester was used for conjugation without further purification.

Example 12: Compound XI

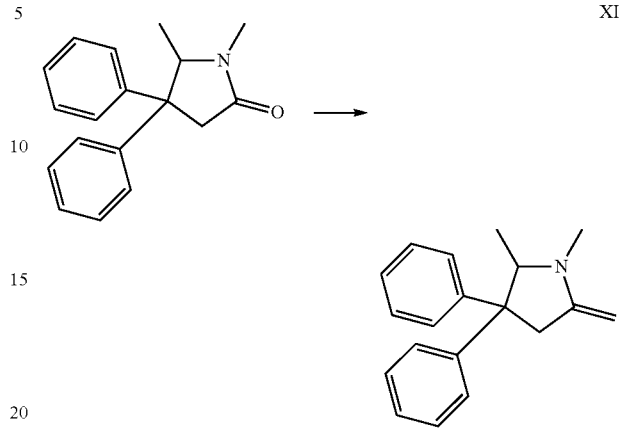

Solid 1,5-dimethyl-3,3-diphenyl-pyrrolidin-2-one # (1.135 mmol) was placed in a round bottom flask containing a stir-bar. The flask was sealed with a rubber septum and placed under a positive Argon atmosphere then Methyllithium (3.4 mmol) was added and stirred for 10 minutes. The mixture was cooled using an ice bath then quenched with ice chips (piece-wise addition). After bubbling stopped, the mixture was extracted with ethyl acetate (~20 mL*2) and DI water (~20 mL). The combined organic layer was separated, washed with brine (~20 mL), dried over Na$_2$SO$_4$ (~10 g) for ~10 minutes, filtered, and evaporated to dryness to give a light yellow oil. The product was dried under high-vac to give 1,5-dimethyl-2-methylene-3,3-diphenyl-pyrrolidine as a light yellow oil. Isolated Yield=103%. NMR (DMSO-d$_6$): δ 7.13-7.30 (m, 9H), 3.67 (S, 1H), 2.98-3.02 (m, 2H), 2.63 (s, 3H), 2.59 (dd, J$_1$=10.5 Hz, J$_2$=24.4 Hz, 1H), 2.28 (dd, J$_1$=18 Hz, J$_2$=24.4 Hz, 1H), 1.10 (d, J=12 Hz, 3H).

Example 13: Compound XII

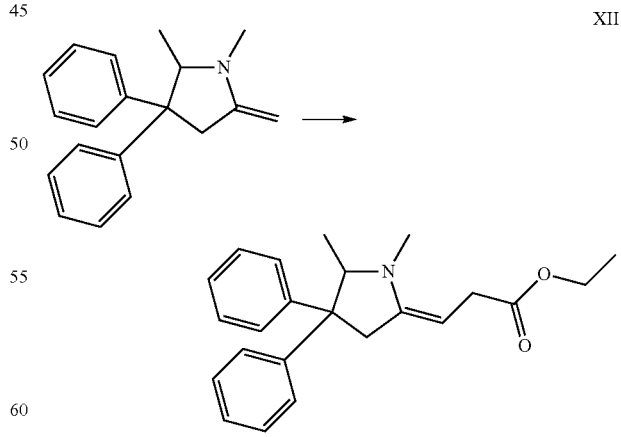

1,2-dimethyl-5-methylene-3,3-diphenylpyrrolidine # (0.91 mmol) was dissolved in dry acetonitrile (5 mL) and followed by ethyl iodoacetate (1.9 mmol). The mixture was placed under argon then heated at 40° C. for 14 hours. The reaction mixture was evaporated to dryness and the residue partitioned between ethyl acetate (15 mL) and water (10 mL). The aqueous layer was back extracted with ethyl acetate (15 mL) then with DCM (10 mL). The combined organic layers were washed with brine (10 mL), dried over $Na_2SO_4$, filtered, evaporated to dryness, and purified via silica gel chromatography. The product was dried under vacuum overnight to give 1-chloro-2-(3-ethoxy-3-oxopropyl)-1,5-dimethyl-3,3-diphenylpyrrolidin-1-ium-2-ide as an off-white foam. Isolated Yield=50%. TLC: Rf=0.28 in 10% MeOH/DCM. NMR (DMSO-$d_6$): δ 7.42-7.48 (m, 6H), 7.29-7.31 (m, 2H), 7.24 (d, J=14.1 Hz, 2H), 4.61 (q, J=13.8 Hz, 1H), 3.95 (q, J=14.3 Hz, 2H), 3.65 (s, 3H), 3.26 (dd, $J_1$=14.9 Hz, $J_2$=27.7 Hz, 1H), 3.03-3.16 (m, 2H), 2.54 (dd, $J_1$=15.2 Hz, $J_2$=27.8 Hz, 1H), 1.98-2.05 (m, 1H), 1.72-1.79 (m, 1H), 1.44 (d, J=13.1 Hz, 3H), 1.09 (t, J=14.1 Hz, 3H).

Example 14: Compound XIII

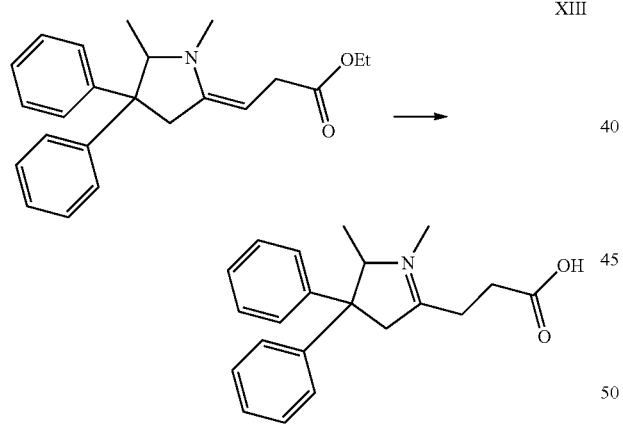

Ethyl 3-(1,5-dimethyl-4,4-diphenylpyrrolidin-2-ylidene)propanoate # (0.401 mmol) was dissolved in methanol (6 mL). 1 N sodium hydroxide (2 mL) was added and the mixture heated at 60° C. for 2.5 hours. Once cooled, the solution was concentrated to remove the methanol at which time the remaining aqueous material was acidified using aqueous 1 N HCl (4 mL). The solution was concentrated to dryness then dissolved in dichloromethane (10 mL). Bath sonication was used to help dissolve the product and the solids subsequently removed via filtration. The solids were rinsed with dichloromethane (5 mL) and the collected filtrate was evaporated to dryness providing a yellow foam. Isolated Yield=95%. TLC: Rf=0.48 in 10:2:1 IPA/$NH_3$/$H_2O$. NMR (DMSO-$d_6$): δ 12.50 (bs, OH), 7.42-7.50 (m, 6H), 7.30 (dd, $J_1$=3.9 Hz, $J_2$=16 Hz, 2H), 7.29 (dd, $J_1$=2.8 Hz, $J_2$=17 Hz, 2H), 4.61 (sept, J=13.8 Hz, 1H), 3.64 (s, 3H), 3.26 (dd, $J_1$=15 Hz, $J_2$=27.6 Hz, 1H), 2.98-3.10 (m, 2H), 2.54 (dd, $J_1$=15 Hz, $J_2$=27.5 Hz, 1H), 1.88-1.95 (m, 1H), 1.62-1.69 (m, 1H), 1.45 (d, J=17.2 Hz, 3H). LC/MS: 322 (M/z).

Example 15: Compound XIV

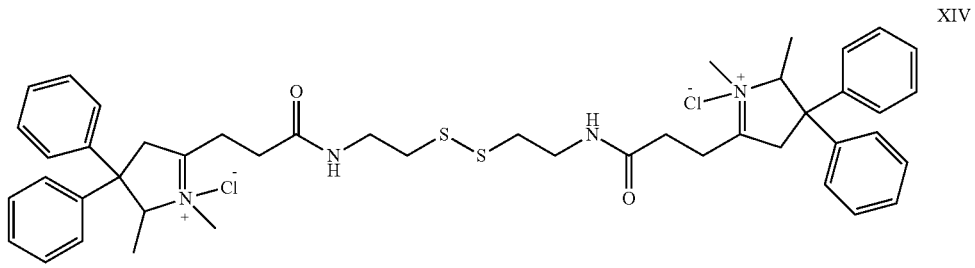

The propanoic acid (0.140 mmol) was dissolved in dry methylene chloride (10 mL) and stirred. Cystamine dihydrochloride (0.0861 mmol), HATU (0.179 mmol) and DIEA (0.464 mmol) were added in succession and stirred for 3 hours at room temperature. The mixture was partitioned between dichloromethane (10 mL) and deionized water (10 mL). The organic layer was collected, washed with brine (10 mL), dried over $Na_2SO_4$ (5 g), filtered, evaporated to dryness, and purified via silica gel chromatography. The product was purified via silica gel chromatography. The viscous oil identified as the product was re-dissolved in dichloromethane (5 mL) then treated with 1 N HCl in ether (1.5 mL) at which time an off-white precipitate formed. The mixture was evaporated to dryness to give the bis-chloride salt as an off-white solid. Isolated Yield=46%. TLC: Rf=0.35, 5% MeOH/2% $NH_3H_2O$/DCM. NMR (DMSO-$d_6$): δ 8.08 (t, J=11.1 Hz, 2H), 7.42-7.48 (m, 12H), 7.29 (m, 4H), 7.4 (dd, $J_1$=3.0 Hz, $J_2$=14.0 Hz, 4H), 4.60 (sept, J=13.6 Hz, 2H), 3.63 (s, 6H), 3.18-3.28 (m, 6H), 2.98-3.10 (m, 4H), 2.65 (t, 4H), 2.52) dd, $J_1$=15.2 Hz, $J_2$=27.8 Hz, 2H), 1.87-1.93 (m, 2H), 1.56-1.62 (m, 2H), 1.44 (d, J=13.2 Hz, 6H). LC/MS: 322 (M/z).

Example 16: Compound XV

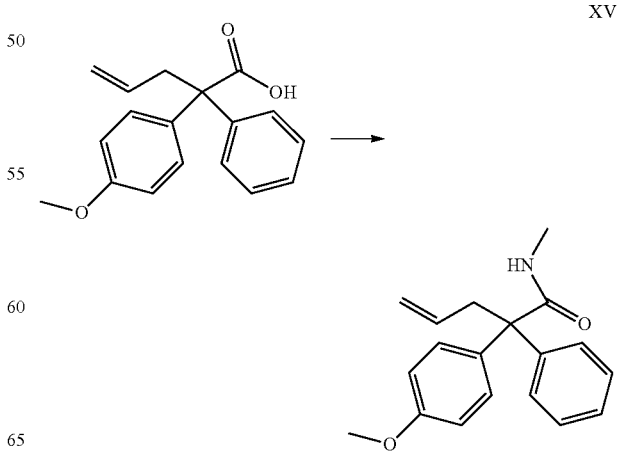

2-(4-methoxyphenyl)-2-phenyl-pent-4-enoic acid # (3.93 mmol) was dissolved in anhydrous THF (10 mL). To the mixture was added HATU (4.3 mmol), methylamine hydrochloride (10 mmol), diisopropylethylamine (17 mmol), and then heated at 60° C. for 3 hours under Argon. The yellow suspension was cooled to room temperature and the solvents removed. The residue was partitioned in a separatory funnel between ethyl ether (100 mL) and sat. NaHCO₃ (100 mL). The aqueous layer was washed with ethyl ether (100 mL). The organic extracts were combined, washed with brine (100 mL), dried over Na₂SO₄ (~30 g), filtered, then concentrated in vacuo. Provided an orange oil which was purified via silica gel column chromatography. Isolated Yield=92%. NMR (DMSO-d₆): δ 7.27-7.30 (m, 2H), 7.19-7.22 (m, 4H), 7.11-7.14 (m, 2H), 6.84-6.87 (m, 2H), 5.44-5.55 (m, 1H), 4.84-4.90 (m, 2H), 3.73 (s, 3H), 3.07 (d, J=13.7 Hz, 2H), 2.56 (d, J=8.9 Hz, 3H).

Example 17: Compound XVI

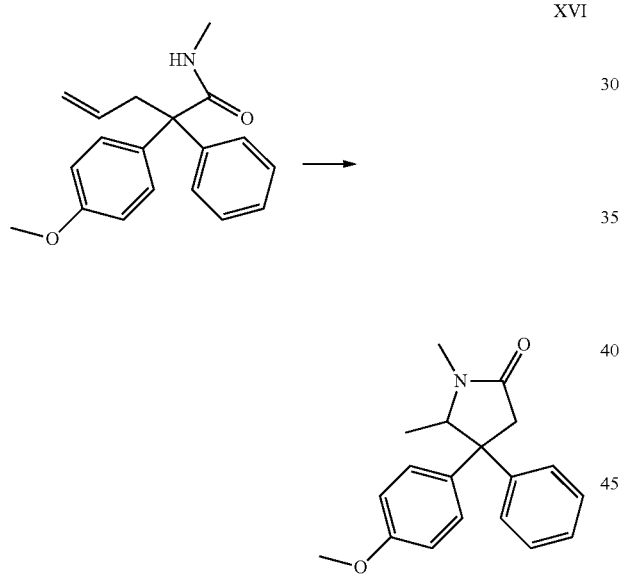

N-methyl-3,3-diphenylpent-4-enamide (3.59 mmol) was dissolved in anhydrous DMF (10 mL). Potassium t-butoxide (8.7 mmol) was added under argon then stirred and heated at 100° C. for 14 hours. The mixture was cooled to room temperature then partitioned between ethyl acetate (2*100 mL) and Di water (100 mL). The organic layers were combined, washed with brine (100 mL), dried over Na₂SO₄ (20 g), filtered, and evaporated to dryness. The crude oil was purified via silica gel column chromatography to give the desired product as a light yellow oil. Isolated Yield=81%. TLC: NMR (DMSO-d₆): δ 7.18-7.30 (m, 7H), 6.83-6.88 (m, 2H), 3.71 (d, J=9.7 Hz, 3H), 3.42-3.46 (m, 1H), 2.94-3.07 (m, 1H), 2.76 (d, J=11.0 Hz, 3H), 2.05-2.17 (m, 1H), 1.19 (t, J=11.7 Hz, 3H).

Example 18: Compound XVII

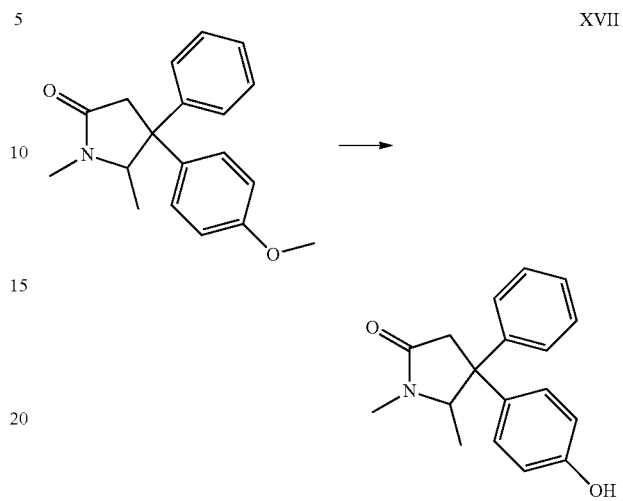

3-(4-methoxyphenyl)-1,5-dimethyl-3-phenyl-pyrrolidin-2-one (2.9 mmol) was dissolved in dichloromethane (5 mL), placed under argon, then cooled using a dry ice/acetone bath. Boron tribromide (6.7 mmol, 1 M in DCM) was added drop-wise giving rise to a dark colored solution. The reaction was stirred at room temperature for 2 hours then cooled using an ice bath. Deionized water (50 mL) was added and stirred for 20 min. The mixture was extracted with dichloromethane (50 mL×2) then the organic layers combined, washed with brine (50 mL), dried over Na₂SO₄ (20 g), filtered, and evaporated to dryness yielding the phenol as a purple foam. Yield=93%. NMR (DMSO-d₆): δ 9.30 (BS, OH), 7.30-7.14 (m, 5H), 7.07-7.11 (m, 2H), 6.65-6.69 (m, 2H), 3.42 (m, 1H), 2.95 (td, J₁=11.6 Hz, J₂=26 Hz, J₃=37.3 Hz, 1H), 2.75 (d, J=8.2 Hz, 3H), 1.99-2.15 (m, 1H), 1.19 (t, J=12.2 Hz, 3H).

Example 19: Compound XVIII 3-(4-hydroxyphenyl)-1,5-dimethyl-3-phenyl-pyrrolidin-2-one # (0.3198 mmol) was dissolved in acetonitrile (3 mL) under argon. To the mixture was added cesium carbonate (0.48 mmol) and N-bromoacetyl-HCTL (0.383 mmol). The reaction was purged with argon then stirred for 5 hours at 50 C. The reaction was cooled to room temperature. Additional N-bromoacetyl-HCTL (0.256 mmol) was added to the reaction, purged with argon, and stirred at 50 C for an additional 8 hours.

The reaction was cooled to room temperature, diluted with ethyl acetate (10 mL), washed with 10 mL of deionized water. The layers were separated and the aqueous was extracted with ethyl acetate (10 mL). The organic layers were combined, washed with brine (10 mL), dried over $Na_2SO_4$ (5 g, 20 min), filtered, and concentrated. Purification via silica gel chromatography provided the product was isolated as a light yellow foam. Isolated Yield=32%. TLC: Rf=0.50 in 100% ethyl acetate. NMR (DMSO-$d_6$): δ 8.46 (d, J=16.8 Hz, 1H), 7.16-7.30 (m, 7H), 6.88-6.92 (m, 2H), 4.69 (m, 1H), 4.50 (m, 2H), 3.39-3.45 (m, 2H), 3.27-3.32 (m, 2H), 2.94-3.05 (m, 1H), 2.76 (d, J=9.0 Hz, 3H), 2.49 (q, J=11.0 Hz, 1H), 2.06-2.30 (m, 2H), 1.19 (d, J=12.7 Hz, 3H). MS(ESI) m/z: $[M+H]^+$=439.6.

Example 20. Compound XIX

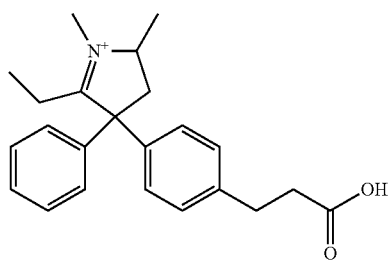

XIX

A general scheme for the synthesis of compound XIX is presented in FIG. 1.

2-phenyl-2-(p-methoxy)phenyl-acetonitrile: to a three neck round bottom flask were taken TosMIC (5 g) and DMSO (23 ml) at r.t.; stirred and cooled to 0° C. under nitrogen protection. To the solution was added tBuOK powder (10 g); stirred for 5 min., anhydrous MeOH (870 µl) was added to the dark solution followed by addition of 4-methoxybenzophenone (3.8 g); warmed up to r.t.; stirred overnight. 400 ml water was added to the solution to quench the reaction. pH of the solution was adjusted to 6 and stirred for 15 min.; brown precipitates was collected; rinsed with water. The solid was recrystallized twice with ethanol to afford 2-phenyl-2-(p-methoxy)phenyl-acetonitrile (off-white solid; 0.7 g).

EMDP-OMe: to a three neck round bottom flask were taken 2-phenyl-2-(p-methoxy)phenyl-acetonitrile (1.4 g); anhydrous THF (10 ml) under nitrogen protection. EtMgBr in ether (3.0M; 2.3 ml) was added; stirred at r.t. for 15 min, methyl aziridine (1.17 ml) in 5 ml THF was added to the solution; stirred at r.t. for 30 min; EtMgBr (9.2 ml) was added; stirred at r.t. overnight. Cooled to 0° C.; 50 ml of 1N HCl was added to the solution; extracted with dichloromethane; rota vapored to give a sticky solid. 7 ml of concentrated HCl was added to the residue; heated and kept refluxing for 1 hr; cooled to r.t.; 70 ml water was added to the solution, extracted with EtOAc, back extracted with 1N HCl; combined; extracted with dichloromethane; washed with saturated $NaHCO_3$ solution and water; dried with $MgSO_4$; filtered and evaporated to give a brown oily mixture which was purified to afford EMDP-OMe (1 g).

EMDP-OH: EMDP-OMe (700 mg) was dissolved in $CHCl_2$ (15 ml); cooled to −78° C. under nitrogen protection; $BBr_3$ (1M, 4.8 ml) was added dropwise; kept stirring at r.t. for 2 hours; 10 ml methanol was added to the solution; stirred for 30 min. The solvents were removed in vacuum; 50 ml saturated sodium bicarbonate solution was added to the residue; extracted with $CH_2Cl_2$; washed with water; regular workup to give a brown solid; purified to give pure EMDP-OH (610 mg).

EMDP-OTf: EMDP-OH (50 mg) was suspended in dichloromethane (10 ml); to the mixture was added pyridine (0.35 ml); cooled to 0° C.; $Tf_2O$ (400) was added slowly. Stirred at that temperature for 1 hr. 1N HCl was added to the solution and stirred for 5 min; separated and washed with 5% $NaHCO_3$ solution; regular workup to give a mixture which was purified to afford a reddish EMDP-OTf (15 mg).

EMDP-p-(ethyl)propanoate: EMDP-OTf (180 mg) was dissolved in THF (10 ml); to the solution were added 3-ethoxy-3-oxopropylzinc bromide solution (0.5M in THF); followed by Pd(dppf)$_2$Cl$_2$ (54 mg) under nitrogen protection. Heated and kept refluxing for 3 hr. quenched with water; extracted with ethyl acetate; regular workup to afford a mixture which was purified to give pure EMDP-p-(ethyl) propanoate (140 mg).

EDDP-p-(ethyl)propanoate: EMDP-p-(ethyl)propanoate (100 mg) was dissolved in ACN (5 ml) at r.t.; to the solution was added Me$_2$SO$_4$ (37 µl); stirred at r.t. under nitrogen protection overnight. The solvent was removed in vacuum; purified to afford pure EDDP-p-(ethyl)propanoate (30 mg).

Carboxyethyl-EDDP: EDDP-p-(ethyl)propanoate (30 mg) was dissolved in MeOH (5 ml); to the solution were added water (1 ml) and NaOH pellets (100 mg); stirred at r.t. for 3 hr; MeOH was removed in vacuum; pH was adjusted to 5; water was removed in vacuum; extracted with isopropanol; filtered and rota vapored under a reduced pressure to afford the final product (carboxyethyl-EDDP; 25 mg).

Example 21. Conjugates

An EDDP derivative was used to prepare conjugates to a latex solid phase and to KLH as described below.

Bovine serum albumin ("BSA") and polystyrene latex particles (Interfacial Dynamics) were incubated at 25° C. for 30 minutes at 1-10 mg BSA per mL of latex slurry at 1-10% solids in 25 mM citrate buffer, pH approximately 4. The solution was then brought to approximately neutral pH with 150 mM potassium phosphate/30 mM potassium borate, and incubated for an additional 2 hours at 25° C. The suspension was washed three times by resuspension in 50 mM potassium phosphate/10 mM potassium borate/150 mM sodium chloride at approximately neutral pH followed by centrifugation.

An N-hydroxysuccinimide/maleimide bifunctional poly (ethylene glycol) crosslinker as described in U.S. Pat. No. 6,887,952 was added at 5-500 mg/mL in deionized water to the BSA-latex particles at 1-10% solids. The crosslinker was incubated with the BSA-latex particles at room temperature for 2 hours. Excess crosslinker was removed by centrifugation and resuspension in PBS of the now maleimide-functionalized BSA-latex particles.

The derivative (4-8 mg) was dissolved in 0.8 mL DMF-water solution (70:30 v/v) and 200 µL of 1 M KOH, and was incubated for 10 minutes at room temperature. Then the excess of the base was neutralized with a phosphate/hydrochloric acid buffer to pH 7. Maleimide-functionalized BSA-latex particles were added to the solution containing the EDDP derivative in the presence of 0.1 mM EDTA, and the mixture was incubated at room temperature overnight. KOH was added to maintain the pH at about 7.0. The reaction was stopped in two steps. First by addition of 0.2 mM β-mercaptoethanol and incubation for 30 at room temperature and then by addition of 6 mM N-(hydroxyethyl)maleimide and additional incubation for 30 minutes at room temperature. The EDDP derivative-conjugated latex particles were purified by centrifugation and resuspension in PBS.

Keyhole Limpet Hemocyanin (KLH, Calbiochem #374817, 50 mg/mL in glycerol) was passed through a 40 mL GH25 column equilibrated in 0.1M potassium phosphate, 0.1M borate, 0.15M sodium chloride buffer, pH 7.5 to remove glycerol. A 1.5-fold molar excess of N-ethylmaleimide was added, and the mixture incubated 30 minutes at room temperature. A 200-fold molar excess of sulfo-SMCC (Pierce #22322) from a 50 mM stock in distilled water was added while vortexing. Vortexing was continued for another 30 seconds, followed by incubation for 10 minutes at room temperature. A 100-fold molar excess of SMCC (Pierce #22360) from an 80 mM stock in acetonitrile was added while vortexing. 1M KOH was added to maintain a pH of between 7.2 and 7.4. The mixture was stirred at room temperature for 90 minutes. After 90 minutes incubation, KLH-SMCC was purified by gel filtration using a GH25 column equilibrated in 0.1M potassium phosphate, 0.02M borate, 0.15M sodium chloride buffer, pH 7.0.

The EDDP derivative (4-8 mg) was dissolved in 0.8 mL DMF-water solution (70:30 v/v) and 200 µL of 1 M KOH, and was incubated for 10 minutes at room temperature. The excess of the base was neutralized with a phosphate/hydrochloric acid buffer and pH brought to 7. Then, a 2-fold molar excess of derivative (based on the concentration of SMCC in a particular batch of KLH-SMCC) was added to KLH-SMCC, and the mixture stirred for 90 minutes at room temperature. Conjugates were purified by exhaustive dialysis in PBS.

Example 22. Antibodies

Following immunization with the KLH-conjugated derivative, phage display antibody libraries were constructed and enriched using biotin-conjugated EDDP derivative and magnetic streptavidin latex as generally described in U.S. Pat. No. 6,057,098. The antibody phage library was selected, transferred into a plasmid expression vector and electro-porated into bacterial cells. Simultaneous negative selection was performed with methadone to select against antibodies binding to undesired epitopes.

The bacterial cells from each antibody library were streaked on agar to generate colonies. The colonies, coding for monoclonal antibodies, were used to inoculate culture medium in individual wells in 96-well plates. The liquid cultures were grown overnight and used to generate frozen cell stocks. The frozen cell stocks were used to generate duplicate 96-well plate cultures, followed by expression and purification of the monoclonal antibodies in soluble form in microgram quantities. Competitive assays for EDDP were developed with selected antibodies.

Example 23. Cross Reactivity

Cross reactivity to methadone metabolites and other common structurally related compounds were evaluated using the antibodies as described with reference to Example 22. Immunoassays were constructed using the antibodies of Example 22, configured to operate in a competitive mode immunoassay format, in which the analogue compounds of the invention were compared with other related compounds for cross reaction against EDDP. Labeled EDDP conjugates were prepared for use as the detectable species. Aliquots of labeled EDDP at 100 ng/mL were incubated in the presence of competing compound with the antibody of the invention, and the level of interaction of the competitor compound determined as a reduction in measured signal compared with the situation where only EDDP was present. The results are provided in Table 1.

TABLE 1

| Analyte | Conc (ng/mL) | % Cross-Reactivity |
| --- | --- | --- |
| EDDP | 100 | 100.00 |
| Methadone | 700,000 | 0.01 |
| EMDP | 1,000,000 | <0.01 |
| Chlorpromazine | 90,000 | 0.11 |
| Diphenhydramine | 1,000,000 | 0.01 |
| Methylphenidate | 100,000 | 0.10 |
| Doxylamine | 1,000,000 | <0.01 |
| LAAM | 1,000,000 | <0.01 |
| (±)-alpha methadol | 1,000,000 | 0.01 |
| (−)-iso-methadone | 100,000 | <0.1 |

The data demonstrate the high specificity of the antibody for EDDP. With many of the competing species being applied at an excess of 10,000 to 1 over EDDP, there was no detectable cross reaction. The data clearly indicate the specificity of the antibodies of the invention for EDDP. An exemplary immunoassay format is described in Wang et al., J. Anal. Toxicol. 35: 108-112 (2011).

Figure 2:
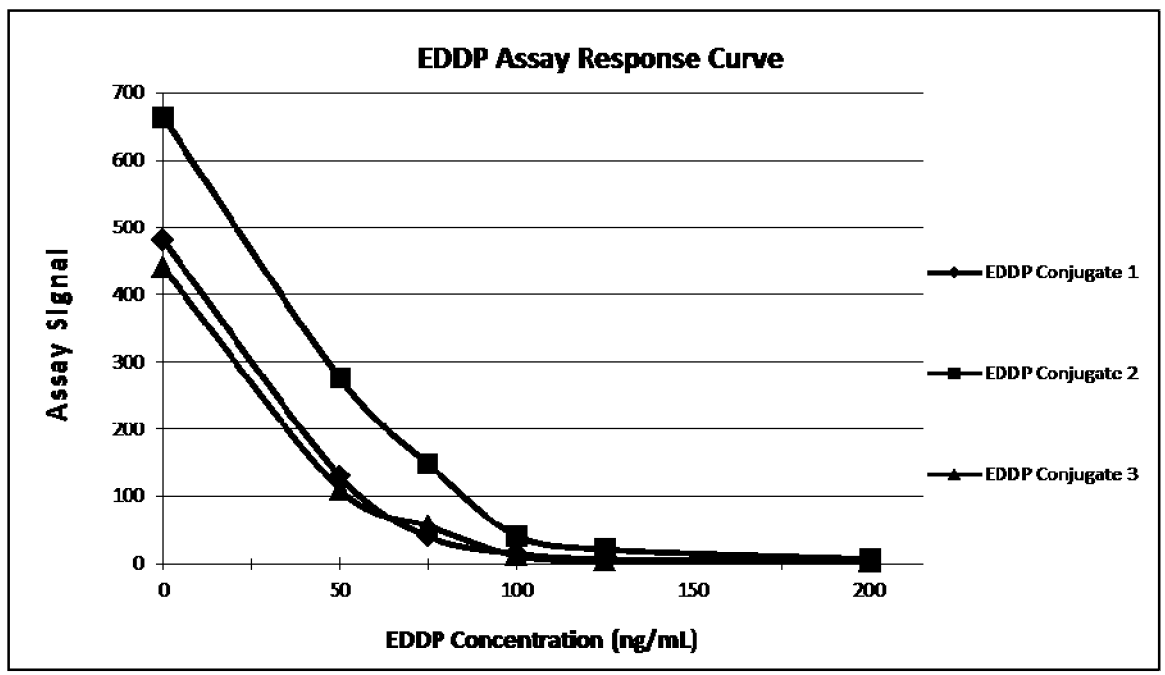
FIG. 2 depicts performance of an exemplary EDDP assay of the invention.

The data shown in FIG. 2 depict an assay performance curve generated using several EDDP conjugates when incubated with the antibody of the invention in the presence of increasing EDDP concentrations. A reduction in signal occurs as the EDDP conjugate is displaced from the antibody by native EDDP at the indicated concentration.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:
1. A compound, cation or salt thereof, said compound or cation having a formula:

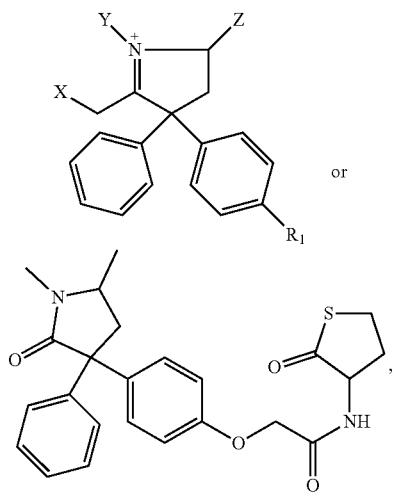

or

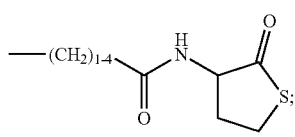

wherein R1 is —CH$_2$—R2, where R2 is:
(a) a linkage chemistry that provides a terminal functional moiety selected from the group consisting of a maleimide, an alkyl halide, an aryl halide, an alpha-haloacyl, an aryl, a pyridyl disulfide, a carbonyl, a carboxyl, a thiol, a thioester, disulfide, and a cyclic thiolactone; or
(b) —(CH$_2$)$_{1-4}$—S—C(O)—CH$_3$, —(CH$_2$)$_{1-4}$—C(O)—OH, —(OCH$_2$CH$_2$)$_n$—R$_3$ where n is between 0 and 25, or

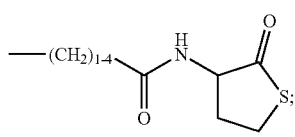

X is H, C$_{1-6}$ saturated alkyl straight or branched chain, C$_{1-6}$ unsaturated alkyl straight or branched chain, C$_{1-6}$ alkoxy, or haloalkyl;

Y is H, C$_{1-6}$ saturated alkyl straight or branched chain, C$_{1-6}$ unsaturated alkyl straight or branched chain, C$_{1-6}$ alkoxy, or haloalkyl; and Z is H, C$_{1-6}$ saturated alkyl straight or branched chain, C$_{1-6}$ unsaturated alkyl straight or branched chain, C$_{1-6}$ alkoxy, or haloalkyl.

2. The compound, cation or salt thereof according to claim 1, wherein the compound is selected from the group consisting of

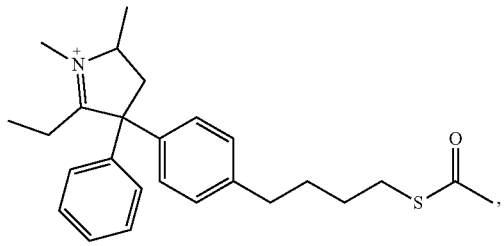

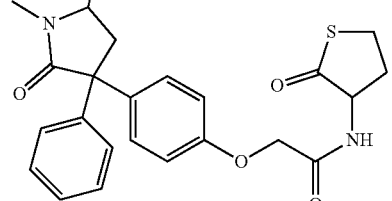

, and

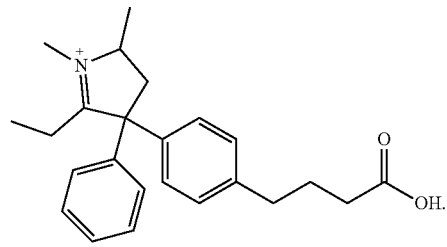

3. A conjugate comprising the compound, cation or salt thereof according to claim 1, wherein said compound or salt thereof is covalently bound through the terminal functional moiety to a corresponding coupling site on a protein, polypeptide, detectable label, nucleic acid, or solid phase.

4. The conjugate according to claim 3, wherein said terminal functional moiety is a maleimide.

5. The conjugate according to claim 3, wherein said terminal functional moiety is an alkyl halide, an aryl halide, an acryl, or an α-haloacyl, wherein the terminal functional moiety reacts with sulfhydryls to form thiol ether bonds.

6. The conjugate according to claim 3, wherein said detectable label is selected from the group consisting of an enzyme, a fluorophore, biotin, avidin, streptavidin, digoxigenin, maltose, oligohistidine, 2,4-dintrobenzene, phenylarsenate, a metal, a fluorescent or colored microsphere, and a fluorescent or colored latex particle.

7. The conjugate according to claim 3, wherein said protein is keyhole limpet hemocyanin, bovine serum albumin, thyroglobulin, ovalbumin, lysozyme, or dextran.

8. The conjugate according to claim 3, wherein said solid phase is selected from the group consisting of a membrane, a cellulose-based paper, a polymeric particle, a latex particle, a paramagnetic particle, a gold particle, a magnetic particle, a metallic particle, a plasmonic particle, a glass substrate, a silicon substrate, a plastic substrate, and a multiple-well plate.

9. A method of preparing a conjugate, said method comprising contacting a compound, cation or salt thereof according to claim 1 with a protein, polypeptide, detectable label, nucleic acid, or solid phase under conditions to provide covalent coupling of said compound, cation or salt thereof to said protein, polypeptide, detectable label, nucleic acid, or solid phase through a reactive moiety on the compound or salt thereof.

10. A method of stimulating an immune response to 2-ethylidene-1,5-dimethyl-3,3-diphenylpyrrolidine (EDDP), said method comprising immunizing an animal with a conjugate of claim 3.

11. The method according to claim 10, further comprising isolating an antibody that specifically binds EDDP.

12. The method according to claim 11, wherein said antibody is isolated directly from said animal.

13. A method of determining a concentration of 2-ethylidene-1,5-dimethyl-3,3-diphenylpyrrolidine (EDDP) in a sample, said method comprising:
   performing a competitive binding assay using a conjugate according to claim 3 that competes with EDDP for binding to an antibody, wherein the conjugate comprises a covalently bound detectable label; measuring a signal produced by said detectable label; and
   determining a concentration of EDDP in said sample using said signal.

* * * * *